United States Patent
Ho et al.

(10) Patent No.: US 9,889,225 B2
(45) Date of Patent: Feb. 13, 2018

(54) METHOD FOR BONE FORMATION BY ADMINISTERING POLY(LACTIC-CO-GLYCOLIC ACID) CROSS-LINKED ALENDRONATE

(71) Applicant: KAOHSIUNG MEDICAL UNIVERSITY, Kaohsiung (TW)

(72) Inventors: Mei-Ling Ho, Kaohsiung (TW); Je-Ken Chang, Kaohsiung (TW); Rajalakshmanan Eswaramoorthy, Kaohsiung (TW); Shun-Cheng Wu, Kaohsiung (TW); Yao-Hsien Wang, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 14/614,718

(22) Filed: Feb. 5, 2015

(65) Prior Publication Data
US 2015/0157762 A1 Jun. 11, 2015

Related U.S. Application Data

(63) Continuation-in-part of application No. 13/446,827, filed on Apr. 13, 2012, now abandoned, which is a continuation-in-part of application No. 12/860,377, filed on Aug. 20, 2010, now abandoned.

(51) Int. Cl.
| | |
|---|---|
| *A61L 27/18* | (2006.01) |
| *A61L 27/54* | (2006.01) |
| *A61L 27/56* | (2006.01) |
| *C08J 9/26* | (2006.01) |
| *C08G 63/91* | (2006.01) |
| *C12N 5/0775* | (2010.01) |

(52) U.S. Cl.
CPC .............. *A61L 27/18* (2013.01); *A61L 27/54* (2013.01); *A61L 27/56* (2013.01); *C08G 63/912* (2013.01); *C08J 9/26* (2013.01); *C12N 5/0667* (2013.01); *A61L 2430/02* (2013.01); *C08J 2201/0446* (2013.01); *C08J 2207/10* (2013.01); *C08J 2367/04* (2013.01); *C12N 2500/42* (2013.01); *C12N 2501/999* (2013.01); *C12N 2533/40* (2013.01); *C12N 2537/10* (2013.01); *Y10T 428/2982* (2015.01)

(58) Field of Classification Search
None
See application file for complete search history.

(56) References Cited

U.S. PATENT DOCUMENTS

| | | | | |
|---|---|---|---|---|
| 5,462,932 | A * | 10/1995 | Brenner | A61K 31/663 514/108 |
| 2009/0060969 | A1* | 3/2009 | Mikos | A61F 2/18 424/422 |
| 2009/0148527 | A1* | 6/2009 | Robinson | A61K 9/0048 424/484 |
| 2011/0085979 | A1* | 4/2011 | Satchi-Fainaro | A61K 31/787 424/9.1 |

OTHER PUBLICATIONS

Pignatello et al., A novel biomaterial for osteotropic drug nanocarriers: synthesis and biocompatibility evaluation of a PLGA-ALE conjugate; Nanomedicine, vol. 4, No. 2, pp. 161-175, 2009.*

* cited by examiner

*Primary Examiner* — Addison D Ault
(74) *Attorney, Agent, or Firm* — Hannah M. Tien

(57) ABSTRACT

A method for bone regeneration which comprises administering a short term release composition into a bone area of a subject in need thereof, wherein the composition comprises a poly(lactic-co-glycolic acid) cross-linked alendronate (PLGA-ALN), wherein the composition releases the alendronate into the bone area, wherein the bone tissue of the bone area is exposed in situ to a therapeutically effective amount of the alendronate over 9 days.

6 Claims, 19 Drawing Sheets

PLGA

PLGA-ALN-3D

PLGA

PLGA-ALN-M (a)

(b)

(c)

(d)

(a)

(b)

METHOD FOR BONE FORMATION BY ADMINISTERING POLY(LACTIC-CO-GLYCOLIC ACID) CROSS-LINKED ALENDRONATE

This application is a Continuation-in-part of the pending U.S. patent application Ser. No. 13/446,827 filed on Apr. 13, 2012, which is a Continuation-in-part of the U.S. patent application Ser. No. 12/860,377 filed on Aug. 20, 2010, now abandoned, that is incorporated herein by reference in its entirety.

Although incorporated by reference in its entirety, no arguments or disclaimers made in the parent application apply to this divisional application. Any disclaimer that may have occurred during the prosecution of the above-referenced application(s) is hereby expressly rescinded. Consequently, the Patent Office is asked to review the new set of claims in view of the entire prior art of record and any search that the Office deems appropriate.

FIELD OF THE INVENTION

The present invention relates to a method for bone regeneration which comprises administering a short term release composition into a bone area of a subject in need thereof, wherein the composition comprises a poly(lactic-co-glycolic acid) cross-linked alendronate (PLGA-ALN), wherein the composition releases the alendronate into the bone area, wherein the bone tissue of the bone area is exposed in situ to a therapeutically effective amount of the alendronate over 9 days.

BACKGROUND OF THE INVENTION

The induction factors play a major role in directing stem cells differentiation into tissue specific cells, and thus they can be applied in tissue engineering (Lutolf and Hubbell, Nat Biotechnol, 2005, 23:47-55). Induction factors can be either protein-based or chemical-based (Gaissmaier et al, Injury, 2008, Suppl 1: S88-96; Zur Nieden et al, BMC Dev Biol, 2005, 5:1); however, these induction factors have their drawbacks including expensive, may damage tissues, or difficult to deliver. Therefore, it is important to search new induction factors that can initiate and/or facilitate the differentiation of stem cells thus promote subsequent specific matrices deposition resulting in regeneration in vivo. It has been reported that bone morphogenetic protein-2 (BMP-2) plays an important role in the early stage of differentiation process of adult stem cells into osteoblasts or chondrocytes (Chen et al, Growth Factors, 2004, 22:233-241; Shea et al, J Cell Biochem, 2003, 90:1112-1127; Kato et al, Life Sci, 2009, 84:302-310). Previous reports also showed that BMP-2 induces mesenchymal stem cells differentiation and promotes bone and cartilage repair in-vitro and in-vivo (Gaissmaier et al, Injury, 2008, Suppl 1: S88-96; Zhao et al, J Control Release, 2010, 141:30-37; Diekman et al, Tissue Eng Part A, 2009; Mrugala et al, Cloning Stem Cells, 2009, 11:61-76; Park et al, J Biosci Bioeng, 2009, 108:530-537 Hou et al, Biotechnol Lett, 2009, 31:1183-1189).

Bisphosphonates are the commonly used drugs to treat osteoporosis (Russell, Pediatrics, 2007, 119 Suppl 2:S150-162; Rogers, Curr Pharm, 2003, 9:2643-2658; Fisher et al, Endocrinology, 2000, 141:4793-4796). Alendronate is one of the bisphosphonates acts through interferes the mevalonate pathway in osteoclasts. Recent reports also indicated that alendronate stimulates the mesenchymal stem cells (MSCs) to differentiate into osteogenic lineage.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention can be more fully understood by reading the subsequent detailed description and examples with references made to the accompanying drawing, wherein.

Figure 1:
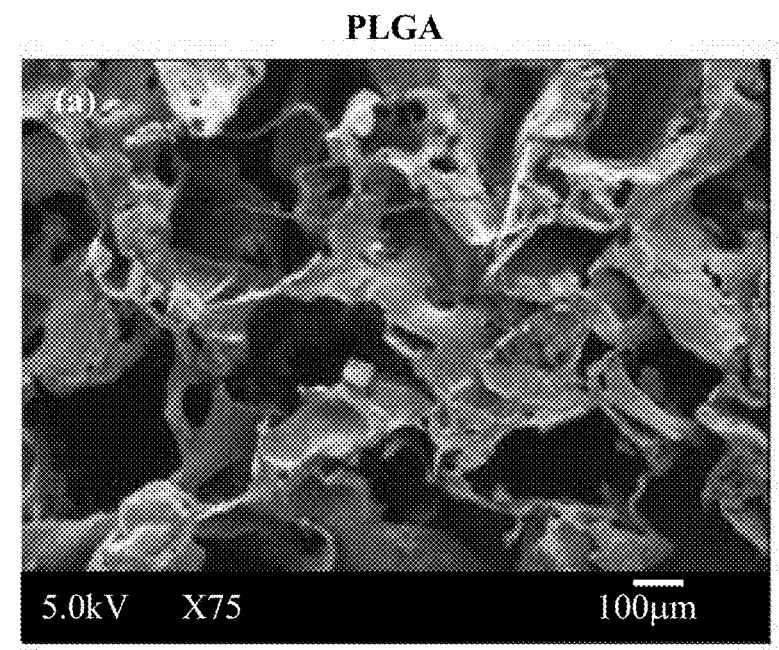
FIG. 1 shows scanning electron microscopy (SEM) image of (a) PLGA, (b) PLGA-ALN scaffold, (c & d) PLGA-ALN microspheres (e) shows the cell adherence in PLGA and PLGA-ALN-3D.
Figure 1:
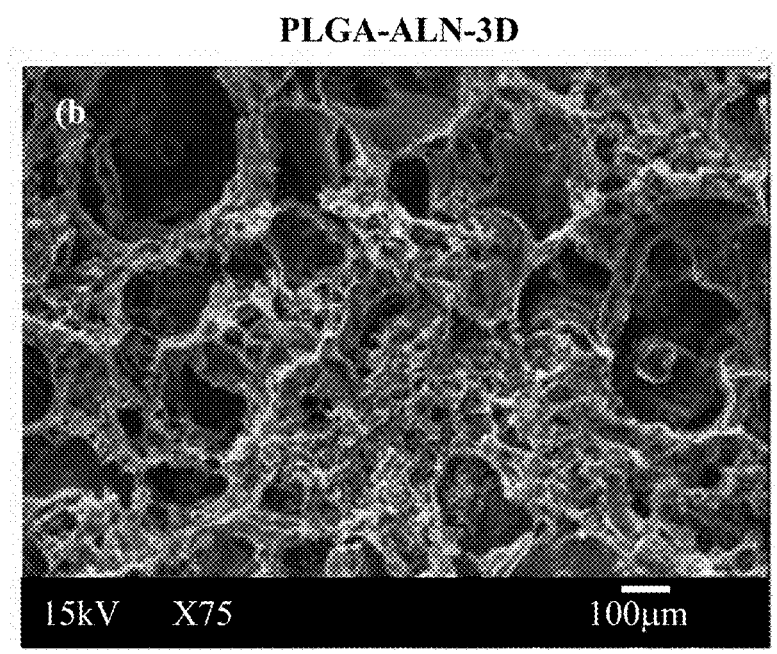
Figure 1:
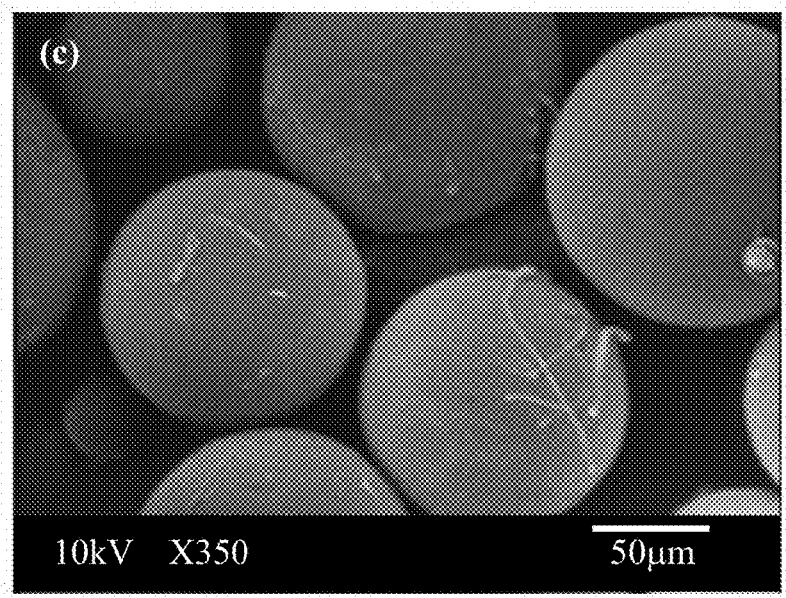
Figure 1:
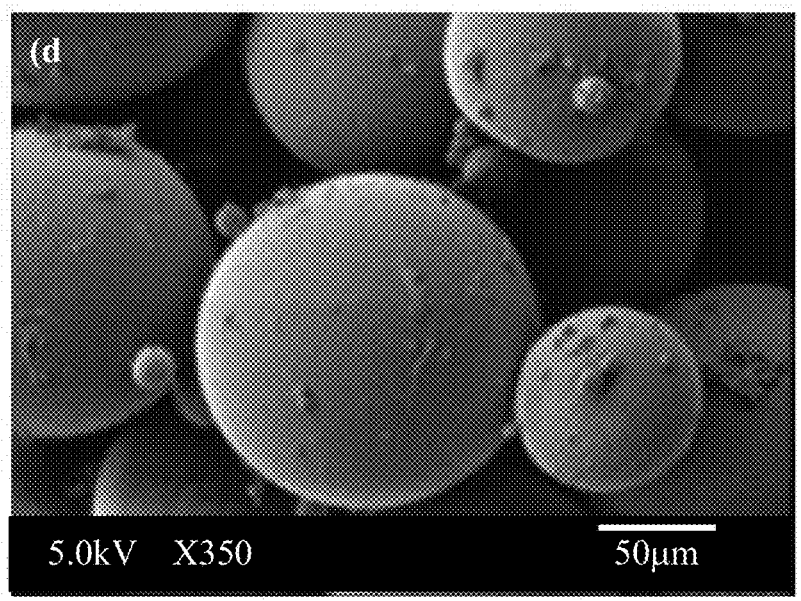
Figure 1:
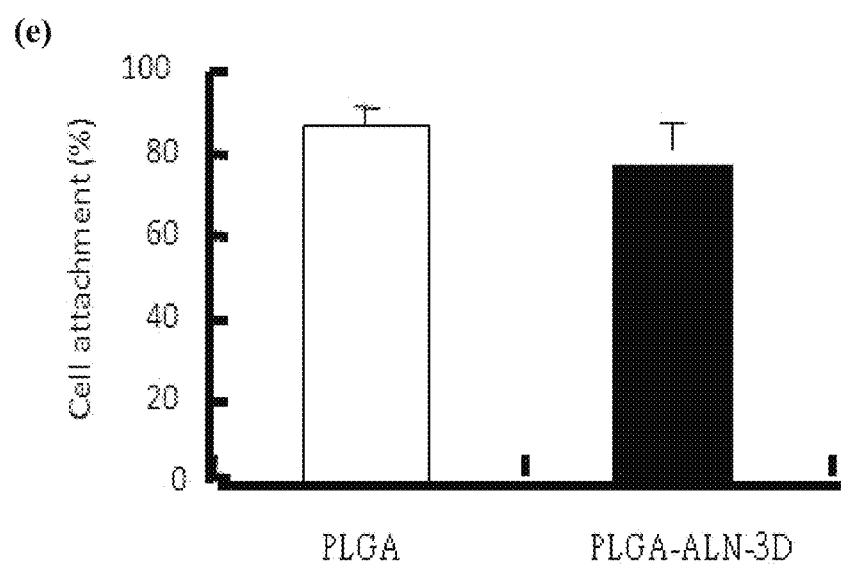

PLGA-ALN 5 mg treatment group; and c. PLGA-ALN 10 mg treatment group. Dark brown indicates the positive staining in the defect site.

SUMMARY OF THE INVENTION

The present invention provides a method for bone regeneration which comprises administering a short term release composition into a bone area of a subject in need thereof, wherein the composition comprises a poly(lactic-co-glycolic acid) cross-linked alendronate (PLGA-ALN), wherein the composition releases the alendronate into the bone area, wherein the bone tissue of the bone area is exposed in situ to a therapeutically effective amount of the alendronate over 9 days.

DETAILED DESCRIPTION OF THE INVENTION

The following description is of the best-contemplated mode of carrying out the invention. This description is made for the purpose of illustrating the general principles of the invention and should not be taken in a limiting sense. The scope of the invention is best determined by reference to the appended claims.

Short term treatment of bisphosphonates on human bone marrow mesenchymal stem cells (BMSCs) and adipose derived stem cells (ADSCs) increases the BMP-2 expression in a time dependent manner. Bisphosphonate also enhances the microenvironment which induces differentiation of MSCs into different lineages. Implantation of alendronate-treated human ADSCs (hADSCs) in rat calvarial defect shows better bone repairmen than those untreated cells. In HA coated dishes, ALN enhances the HA microenvironment which induces chondrogenesis of hADSCs. However, there is still a need for better short term controlled releasing carrier of alendronate for stem cell-based tissue engineering (Cartmell, J Pharm Sci, 2009, 98:430-441).

Natural and synthetic polymeric carriers (micro- and nano-spheres) have been developed as an effective method to control the release of drugs (Cartmell, J Pharm Sci, 2009, 98:430-441; Bhardwaj et al, J Diabetes Sci Technol, 2008, 2:1016-1029; Mundargi et al, J Control Release, 2008, 125:193-209). The excellent biocompatibility and biodegradability makes poly (lactic-co-glycolic acid) (PLGA) and poly (lactic acid) (PLA) more appropriate carriers for the application of drug delivery (Lim et al, J Mater Sci Mater Med, 2009, 20:1669-1675). PLGA modified HA scaffolds shows better chondrogenic effect on hADSCs (Wu et al, Biomaterials, 2010, 31:631-640). Therefore, it suggests that PLGA cross-linked alendronate is better carrier for short term release of alendronate, and has the potential to enhance the differentiation of human adipose derived stem cells (hADSCs).

Pignatello et al. teaches a nanocarrier, PLGA-ALN conjugate, for osteotropic drug delivery (Pignatello et al., A novel biomaterial for osteotropic drug nanocarriers: synthesis and biocompatibility evaluation of a PLGA-ALE conjugate. Nanomedicine, vol. 4 no.2 pp. 161-175, February 2009). Pignatello et al. constructs PLGA-ALN nanoparticles with a mean size of approximately 200-300 nm. Briefly, NHS-PLGA is synthesized as an activated intermediate for coupling of 50:50 PLGA with alendronate, and an equimolar amount of NHS-PLGA is reacted with alendronate. To obtain nanoparticles, the PLGA-ALN conjugate is then dissolved in acetone, DMSO or an acetone/DMSO 1:1 (v/v) mixture and dropped into PBS with stirring; an alternate method is dissolving the PLGA-ALN conjugate in DMSO followed by dialysis against water. By the above synthesis methods, there will be some residual solvents in the final product. However, Acetone, DMSO and a mixture of acetone/DMSO are apoptotic, hepatotoxic and carcinogenic. Therefore, the in vivo application of the resulted nanoparticles is limited. Moreover, the large surface area of nanoparticles makes it hard to provide the ideal release concentration for stem cell differentiation.

Accordingly, the present invention provides a short term controlled release composition which comprises poly(lactic-co-glycolic acid) (PLGA) cross-linked alendronate (ALN). The concentration of released alendronate from the present short term controlled release composition is in the range of $5 \times 10^{-7}$ M to $5 \times 10^{-8}$ M.

In one embodiment, the present short term controlled release composition is constructed into 3D scaffolds (PLGA-ALN-3D) or microspheres (PLGA-ALN-M).

One skill in the art will recognized that surface area of microspheres and pores size and porosity of 3D scaffolds are critical for releasing concentration. The present invention provides microspheres and 3D scaffolds with diameter and pores size in the scale of micrometer. In one embodiment, the PLGA-ALN-3D scaffolds of the short term controlled release composition have pores size of 150-300 μm and average porosity of 85%. In another embodiment, the PLGA-ALN-M microspheres of the short term controlled release composition are 50-100 μm in diameter. In another embodiment, the PLGA-ALN-M microspheres have smooth surface.

The present invention also provides a method for preparing a short term controlled release composition, which comprises the following steps: (a) activating a carboxylic acid end group of PLGA to produce ethyl(dimethylaminopropyl) carbodiimide (EDC)/N-Hydroxysuccinimide (NHS) activated PLGA; and (b) performing cross linking reaction between EDC/NHS activated PLGA and sodium alendronate.

In one embodiment, the carboxylic acid end group of PLGA of the method for preparing a short term controlled release composition is activated by ethyl(dimethylaminopropyl) carbodiimide (EDC)/N-Hydroxysuccinimide (NHS) method.

In another embodiment, the EDC/NHS method of the method for preparing a short term controlled release composition further comprises mixing NHS, EDC and PLGA. NHS and EDC are mixed in a ratio of 3:2. PLGA is dissolved in dichloromethane. The carboxylic acid end group activated PLGA of the EDC/NHS method is precipitated by excess diethyl ether.

In still another embodiment, the cross-linking reaction of the method for preparing a short term controlled release composition further comprising reacting EDC/NHS activated PLGA and sodium alendronate in the same mole ratio. The cross linking reaction is performed in dry dimethysulphoxide.

The present method avoids adverse chemicals for in-vivo usage, such as, but not limited to, acetone, DMSO, dioxane and triethylamine. The short term controlled release composition of the present composition thus has high biocompatibility.

The present invention further provides a method for enhancing stem cell differentiation into osteogenic lineage, which comprises culturing stem cells in micro-environment with PLGA-ALN.

In one embodiment, the PLGA-ALN of the method for enhancing stem cell differentiation into osteogenic lineage is constructed into 3D scaffolds (PLGA-ALN-3D) or microspheres (PLGA-ALN-M). The PLGA-ALN-3D scaffolds have the pores size of 150-300 µm and average porosity of 85%. The PLGA-ALN-M microspheres are 50-100 µm in diameter with smooth surface.

In one embodiment, the stem cells of the method for enhancing stem cell differentiation into osteogenic lineage are adipose derived stem cells (ADSCs) of human origin.

The present invention also provides a method for enhancing stem cell differentiation into chondrogenic lineage, which comprises culturing a population of stem cells in micro-environment with hyaluronan (HA) and PLGA-ALN.

In one embodiment, The PLGA-ALN of the method for enhancing stem cell differentiation in to chondrogenic lineage is constructed into microspheres (PLGA-ALN-M). The PLGA-ALN-M microspheres are 50-100 µm in diameter with smooth surface. The stem cells of the method for enhancing stem cell differentiation into chondrogenic lineage are adipose derived stem cells (ADSCs) of human origin.

PLGA cross-linked ALN enhanced the osteogenic and chondrogenic differentiation of hADSCs under the osteo-induction condition and chondro-induction condition respectively. And the cross linking between PLGA and ALN do not affect the efficiency of ALN. Therefore, PLGA-ALN is a short term controlled release carrier for enhancing osteogenic and chondrogenic differentiation in committed hADSCs for the regeneration of bone and cartilage. The present invention is suitable for application in stem cell based tissue engineering.

As used herein in the specification, "a" or "an" may mean one or more. As used herein in the claim(s), when used in conjunction with the word "comprising", the words "a" or "an" may mean one or more than one.

The present method provides a method for bone regeneration which comprises administering a short term release composition into a bone area of a subject in need thereof, wherein the composition comprises a poly(lactic-co-glycolic acid) cross-linked alendronate (PLGA-ALN), wherein the composition releases the alendronate into the bone area, wherein the bone tissue of the bone area is exposed in situ to a therapeutically effective amount of the alendronate over 9 days.

A "therapeutically effective amount" is an amount effective to enhance stem cells of the bone tissue differentiating into osteogenic cells that form bone. Determination of a therapeutically effective amount is well within the capability of those skilled in the art.

In one embodiment, the subject is an animal. Preferably, the subject is a mammal. Mammals include, but are not limited to, humans, primates, farm animals, sport animals, rodents and pets. More preferably, the subject is a human.

In another embodiment, the alendronate enhances stem cells of the bone tissue differentiating into osteogenic cells that form bone. In a preferred embodiment, the alendronate increases an expression level of a bone morphogenetic protein-2 (BMP-2) to enhance the bone regeneration in the bone tissue. In a more preferred embodiment, the alendronate increases the amount of the BMP-2 in the bone tissue to promote the differentiation of the stem cells of the bone tissues.

In one embodiment, the PLGA-ALN is administered with the stem cell into the bone area.

As used herein, the term "stem cells" comprises mesenchymal stem cells (MSCs). MSCs are multipotent stromal cells that can differentiate into a variety of cell types, including: osteoblasts (bone cells), chondrocytes (cartilage cells), and adipocytes (fat cells). This phenomenon has been documented in specific cells and tissues in living animals and their counterparts growing in tissue culture. In a preferred embodiment, the stem cells are human adipose-derived stem cells (hADSCs).

The bone regeneration is a complex physiological process of bone formation, which can be seen during normal fracture healing, and is involved in continuous remodelling throughout adult life. Bone regeneration is comprised of a well-orchestrated series of biological events of bone induction and conduction, involving a number of cell types and intracellular and extracellular molecular-signalling pathways, with a definable temporal and spatial sequence, in an effort to optimise skeletal repair and restore skeletal function. In the clinical setting, the most common form of bone regeneration is fracture healing, during which the pathway of normal fetal skeletogenesis, including intramembranous and endochondral ossification, is recapitulated.

The bone formation is an essential process in the development of the subject body. It starts during the development of the fetus, and continues throughout childhood and adolescence as the skeleton grows. The bone regeneration comprises an intramembranous ossification or an intracartilanginous ossification (endochondral ossification). The bone formation further comprises a bone remodelling that meanwhile is a life-long process, consisting of resorption (the breaking down of old bone) and ossification (formation of new bone), and is key to shaping the skeleton and to the repair of bone fractures.

By "differentiating" or "differentiation" is meant that the formation of cells expressing markers known to be associated with cells that are more specialized and closer to becoming terminally differentiated cells incapable of further division or differentiation.

In one embodiment, the therapeutically effective amount of the alendronate in the bone tissue sustains in the range of $8 \times 10^{-7}$ M to $1 \times 10^{-8}$ M over 9 days. In a preferred embodiment, the therapeutically effective amount of the alendronate in the bone tissue sustains in the range of $6 \times 10^{-7}$ M to $3 \times 10^{-8}$ M over 9 days. n a more preferred embodiment, the therapeutically effective amount of the alendronate in the bone tissue sustains in the range of $5 \times 10^{-}$M to $5 \times 10^{-8}$ M over 9 days.

In another embodiment, the therapeutically effective amount of the alendronate in the bone tissue sustains in the concentration of $5\text{-}7 \times 10^{-7}$ M at the first and second days after administering.

In one embodiment, the alendronate of the composition is released at 12~20% of the initial alendronate concentration of the composition each day at first two days after administering. In a preferred embodiment, the alendronate of the composition is released at 14~48% of the initial alendronate concentration of the composition each day at first two days after administering. In another embodiment, the alendronate of the composition is released at 4~8% of the initial alendronate concentration of the composition each day over two days after administering.

As used herein, the "short term release" of active agent, such as ALN disclosed herein, means the ALN is sustained released at a short period of time, for example 2-9 days. In a preferred embodiment, the ALN is sustained released over 9 days. In a more preferred embodiment, the ALN is sustained released over 2 days. The term "sustained release" includes continuous or discontinuous, intermittent, linear or non-linear release.

In one embodiment, the composition is formulated to release alendronate in a total daily amount that is in the range of concentration of 0.1-2×10$^{-7}$ M. In a preferred embodiment, the composition is formulated to release alendronate in a total daily amount that is in the range of concentration of 1×10$^{-7}$ M.

The composition comprising the PLGA-ALN can be formulated for administration via sterile aqueous solution or dispersion, aqueous suspension, oil emulsion, water in oil emulsion, site-specific emulsion, long-residence emulsion, sticky-emulsion, microemulsion, nanoemulsion, liposomes, microparticles, microspheres, nanospheres, nanoparticles, minipumps, and with various natural or synthetic polymers that allow for sustained release. The compounds comprising the NRIP can also be formulated into aerosols, tablets, pills, sterile powders, suppositories, lotions, creams, ointments, pastes, gels, hydrogels, sustained-delivery devices, or other formulations used in drug delivery.

As used herein, the "administration" of an agent or drug to a subject includes any route of introducing or delivering to a subject a compound to perform its intended function. Administration includes self-administration and the administration by another.

In one embodiment, the PLGA-ALN is prepared by mixing the PLGA and ALN1 in 1:1.2 molar ratio.

In one embodiment, the PLGA-ALN is constructed into a 3D scaffold (PLGA-ALN-3D). In a preferred embodiment, the PLGA-ALN-3D has the pores size of 150-300 μm and average porosity of 85%.

In another embodiment, the PLGA-ALN is constructed into a microsphere (PLGA-ALN-M). In a more preferred embodiment, the PLGA-ALN-M is 50-100 μm in diameter.

EXAMPLE

The examples below are non-limiting and are merely representative of various aspects and features of the present invention.

Example 1

Isolation and Culture of hADSCs

After obtaining informed consent from all the patients and approval from the Kaohsiung Medical university hospital ethics committee, leftover subcutaneous adipose tissue was acquired from patients undergoing orthopedic surgery. The hADSCs were isolated from human subcutaneous adipose tissue following the previously described method (Fehrer and Lepperdinger, Exp Gerontol, 2005, 40:926-930). The isolated hADSCs were cultured and expanded at 37 C under 5% $CO_2$ in K-NAC medium containing Keratinocyte-SFM (Gibco BRL, Rockville, Md.) supplemented with the EGF-BPE (Gibco BRL, Rockville, Md.), N-acetyl-L-cysteine, L-ascorbic acid 2-phosphate sequimagnesium salt (Sigma, St. Louis, Mo.) and 5% FBS (Fehrer and Lepperdinger, Exp Gerontol, 2005, 40:926-930).

Example 2

Synthesis of PLGA Cross Linked Alendronate (PLGA-ALN)

The fabrication of PLGA-ALN is the two stage process, first the activation of the carboxylic acid end group of PLGA by EDC/NHS method and second is the cross linking reaction. Briefly, 1 g of PLGA (50/50) dissolved in 10 mL of dichloromethane was reacted with 3:2 ratio of NHS and EDC, stirred at room temperature for 12 h. Then, the insoluble dicyclohexylurea was removed by using a 0.45 μm Teflon filter. The activated PLGA polymer product was precipitated by excess diethyl ether, followed by dried under vacuum for 4 h. The PLGA-ALN was prepared by reacting equivalent mole ratio of EDC/NHS activated PLGA with sodium alendronate in dry dimethylsulphoxide stirred under room temperature for 12 h. The final product was precipitated and isolated by adding excess of cold diethyl ether followed by double distilled water. The isolated PLGA-ALN was dried under vacuum and stored at −20° C. till use.

Example 3

Fabrication of Porous PLGA-ALN 3D Scaffolds (PLGA-ALN-3D)

The porous scaffolds for the PLGA-ALN were prepared by the salt leaching method. Briefly, 1:6 weight ratios of PLGA-ALN and combined with NaCl salt (particle size was 300-400 μm) was dissolved in 10 mL of chloroform under magnetic stirring. The gel-like precipitate was mixed completely with sieved salt particulates and was put into 2-mm thick, 5-mm in diameter disc-shaped Teflon molds, followed by a partial evaporation of chloroform at room temperature to obtain a semi-solidified mass. The molds were then immersed in a distilled water solution at room temperature, as well as salt leaching within the polymer/salt matrices. Then the porous polymeric scaffolds were taken out from the molds, washed with distilled water three times, and then dried under vacuum for 1 day.

Example 4

PLGA-ALN Microsphere (PLGA-ALN-M) Preparation and Characterization

The microspheres were fabricated by the o/w emulsion technique (FIG. 1). Briefly, 10% PLGA-ALN polymer solution was prepared by dissolved in dichloromethane (DCM), The single emulsion (o/w) was formed by gradual addition of the polymer solution into the 20 mL of 1% aqueous PVA solution under vigorous stirring. The solution was stirred at room temperature for 30 mins to harden the microspheres, followed by the dichloromethane was evaporated under water suction and then centrifuged to collect solid microspheres. The resultant microspheres were washed with distilled water three times and freeze dried. The overall morphology of the microspheres was examined using scanning electron microscopy (SEM) (Hitachi S3200, Tokyo, Japan) after gold coating of the microsphere samples on a stub and the mean size of the microspheres were measured by particle size analyzer.

Example 5

Evaluation of Release Kinetics in Vitro

In PLGA-ALN, alendronate was chemically cross-linked on the surface of PLGA by covalent bond. Under physiological condition the covalent bond between PLGA and alendronate will break by hydrolysis, which results release of biologically active alendronate from PLGA-ALN. The biological activity of released alendronate was confirmed by in-vitro mineralization test on cells. The released alendronate was quantified by in-vitro spectrophotometric method as reported in Journal of Pharmaceutical and Biomedical Analysis 28 (2002) 1215-1220.

Figure 3:
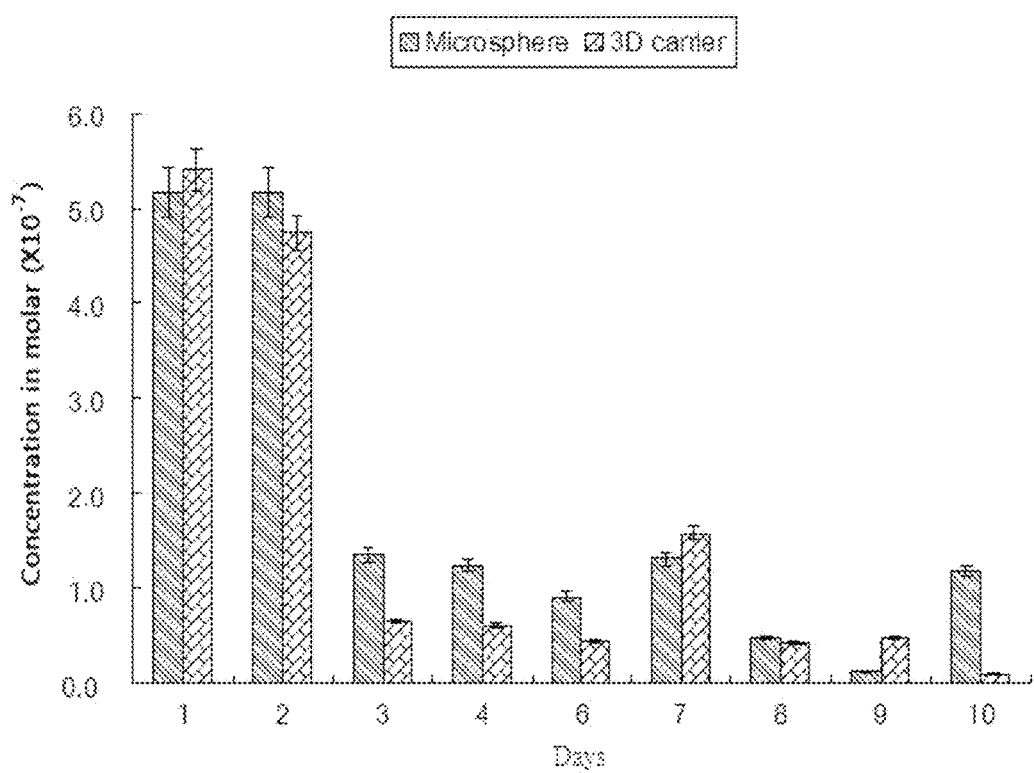
FIG. 3 shows releasing profile for Alendronate from PLGA-ALN carriers.

10 μg PLGA-ALN-M or PLGA-ALN-3D scaffolds were suspended in 1 mL of PBS to form a mixture. The present invention removed 800 μL of PBS every day and replaced the same. 500 μL of PBS sample was collected from the mixture and replaced with fresh PBS at each indicated time point. The concentration of the released alendronate was measured by reported spectrophotometric method (96-well plate reader, U-QUANT, Bio-Tek, Inc.). In FIG. 3, the Initial concentration of Alendronate in 10 mg of PLGA-ALN is $3.2 \times 10^{-5}$ M. The present invention got ~$5.5 \times 10^{-7}$ M in the first two day of burst release followed by 1.2 to $0.5 \times 10^{-7}$ M for the remaining 10 days. The first two days, the present invention got 16% of alendronate release each day. So the two days release is 32% and the remaining days, the invention get ~4 to 8% per day. The conjugation molar ratio is 1:1.2 (PLGA:ALN). 10 mg of PLGA-ALN contains 0.1052 mg of ALN. The actual reaction contain 285 mg of PLGA with 4 mg of ALN.

Results from release kinetics data showed that PLGA-ALN-3D and PLGA-ALN-M were released the effective concentration in the range of $5 \times 10^{-7}$ M to $5 \times 10^{-8}$ M of alendronate for 9 days (with daily average concentration of $1 \times 10^{-7}$ M) (FIG. 3).

Briefly, an iron(III) chloride solution (5 mM) was prepared by dissolving ferric chloride hexahydrate in 2 M perchloric acid (17.5 mL of 11.5 M perchloric acid was diluted with 50 mL water, 0.135 g of ferric chloride hexahydrate was added and the solution was then diluted to volume of 100 ml with water). Freshly prepared 5 mM alendronate solution in 2 M perchloric acid was used as stock solution. To prepare standard solutions, the stock solution was diluted into appropriate concentrations ranging from 8.1 to 162.5 µg/mL with perchloric acid solution. The standard solutions were mixed with ferric chloride solution; their light absorbances at 310 nm were then measured for construction of calibration graph. To measure the alendronate concentration in above PBS samples, 10 µL of samples were taken and analyzed with above-mentioned method against a reagent blank. All measurements were performed under room temperature immediately after solution mixing.

Example 6

Scanning Electron Microscopy (SEM) Examination

The morphological characteristics of PLGA-ALN scaffolds were observed by using scanning electron microscopy (SEM, JEOL, Tokyo, Japan). However, samples were first coated with gold via a sputter-coater at ambient temperature. Micrographs of both scaffolds were taken at 50× and 100×. The overall morphology of the scaffolds was examined after gold coating of the scaffold samples on a stub and the mean pores size of the scaffolds were 150-300 µm, with average porosity of 85% (FIG. 1(a) to (b)). The PLGA-ALN-M was 50-100 µm in diameter with smooth surface (FIG. 1 (c) to (d)).

Example 7

Cell Culture in PLGA-3D and PLGA-ALN-3D Scaffold

Cells/scaffold constructs of PLGA-3D and PLGA-ALN-3D scaffolds with hADSCs were prepared. The PLGA-3D and PLGA-ALN-3D scaffolds were pre-wetted and sterilized with an aqueous solution of 70% (v/v) ethanol according to previous methods (Yoon et al, Biotechnol Bioeng, 2002, 78:1-10; Yoon et al, Biomaterials, 2004, 25:5613-5620), and then placed in 24-well plates. A 100 µl of ($3 \times 10^5$ cells/100 µL) cell suspension was loaded onto the top surface of each pre-wetted scaffold and allowed to penetrate into the scaffold. The cells/scaffold constructs were then incubated at 37° C. under 5% $CO_2$ condition for 4 h for cell adherence. After cell adherence, the cells/scaffold constructs were transferred to a new 24-well plate in order to remove the lost cells at the bottom of the wells, and 1 mL of culture media was added in each new well containing the cells/scaffold construct. standard medium: DMEM containing 10% FBS (Hyclone, Logan, Utah), 1% nonessential amino acids and 100 U/mL penicillin/streptomycin (Gibco-BRL, Grand Island, N.Y.); and Culture media was changed every 2 days and culture plates were shaken during culture. At every indicated time interval, cells/scaffold constructs were collected for further experimental analysis.

Example 8

Cell adherence and viability test in PLGA-ALN-3D and PLGA-3D scaffold

For cell adherence tests, 4h after cells adhere to the PLGA-ALN or PLGA scaffolds, cells/scaffold constructs were rinsed and removed from the 24-well plates. The number of unattached viable cells inside the wells were counted and compared with the control (24-well plate seeded cells without any scaffold) in order to get the number of viable cells attached to each scaffolds within the first 4 h. Colorimetric method, CELLTITER 96 aqueous one solution cell proliferation assay (Promega, Madison, Wis.), was used to count cell numbers, which is a colorimetric method for determining the number of viable cells in culture (Relic et al, J Immunol, 2001, 166:2775-2782). Briefly, the mitochondria activities of the hADSC cultured on wells were detected by the conversion of 3-(4,5-dimethylthiazol-2-yl)-2,5-diphenyltetrazolium bromide (MTS) to formazan as previously described (Relic et al, J Immunol, 2001, 166:2775-2782; Ma et al, Biomaterials, 2007, 28:1620-1628; Magne et al, J Bone Miner Res, 2003, 18:1430-1442), and the quantity of formazan product released into the medium, which is directly proportional to the number of living cells in culture, can be measured by absorbance at 490 nm (Relic et al, J Immunol, 2001, 166:2775-2782). At the indicated time interval, freshly prepared MTS reaction mixture diluted in standard medium at 1:5 (MTS: medium) volume ratio were added to the wells containing the cells and then incubated at 37° C. under 5% $CO_2$ for an additional 4h. After the additional incubation, 100 µL of the converted MTS released into medium from each well was transferred to 96-well plates and the absorbance at 490 nm was recorded with a microplate reader (PATHTECH) using KC junior software. Cell adherence of hADSCs was calculated using the following formula:

Cell adherence (%)=[1−(Cell number unattached to scaffold/Control cell number inside wells)]× 100%

The PLGA-ALN-3D showed the 80% of hADSCs were adhered on the scaffolds, which is significantly similar to PLGA-3D scaffolds (FIG. 1(e)).

Figure 2:
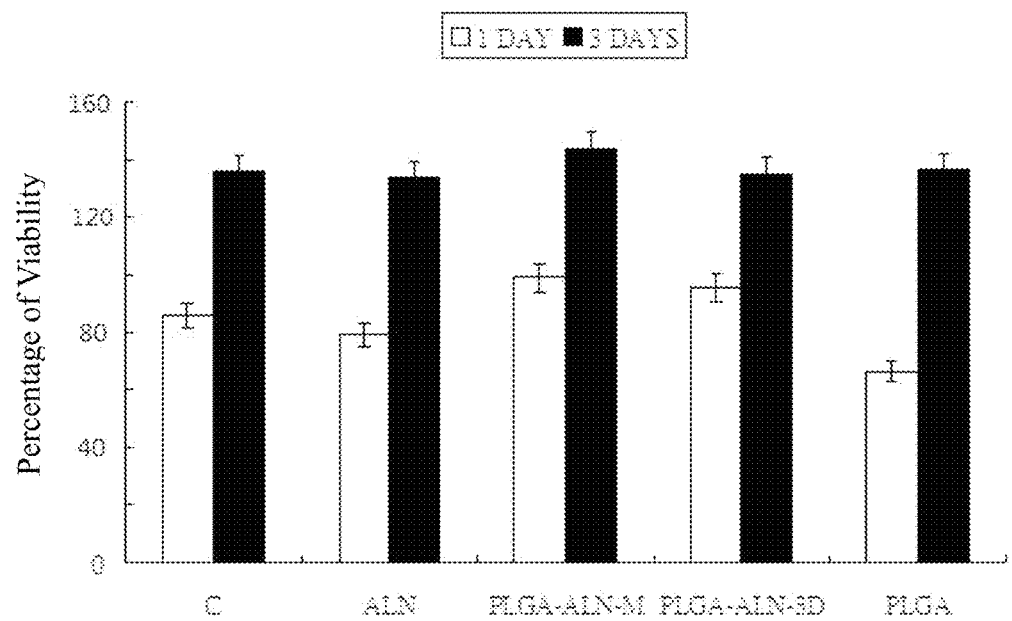
FIG. 2 shows cell viability by 3-(4,5-dimethylthiazol-2-yl)-2,5-diphenyltetrazolium bromide (MTS) analysis.

For cell viability tests, after the cells attached to the scaffold, the cells/scaffold constructs were transferred to a new culture plate and cultured in standard medium for an additional 1, 3, and 5 days at 37° C. under 5% $CO_2$. At every indicated time interval, freshly prepared MTS reaction mixture diluted in standard medium at 1:5 (MTS: medium) volume ratio were added to the wells, and the viable cell numbers within the constructs were assessed. The MTS assay results showed the PLGA-ALN-M or PLGA-ALN-3D treated hADSCs shows no adverse toxic effect at 1 and 3 days (FIG. 2).

Example 9

Osteogenic Differentiation

Figure 4:
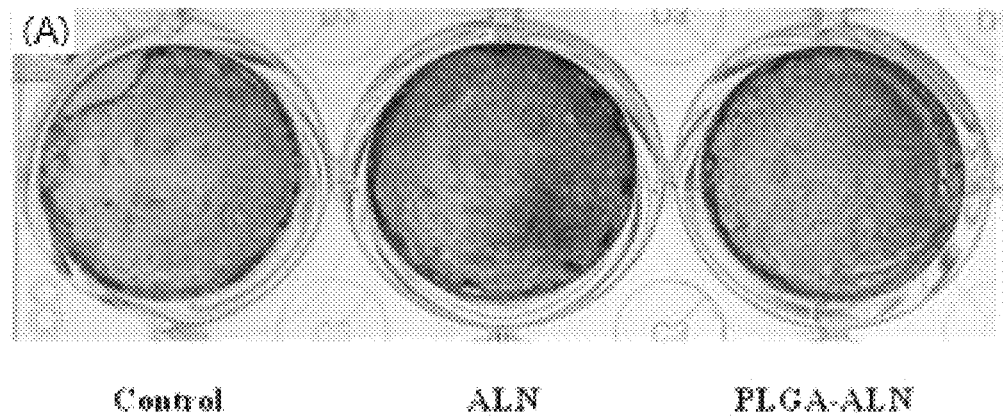
FIG. 4 shows Alizarin red S staining for mineralization (A) and quantification of mineralization in PLGA-ALN-M cultured hADSCs (B).
Figure 4:
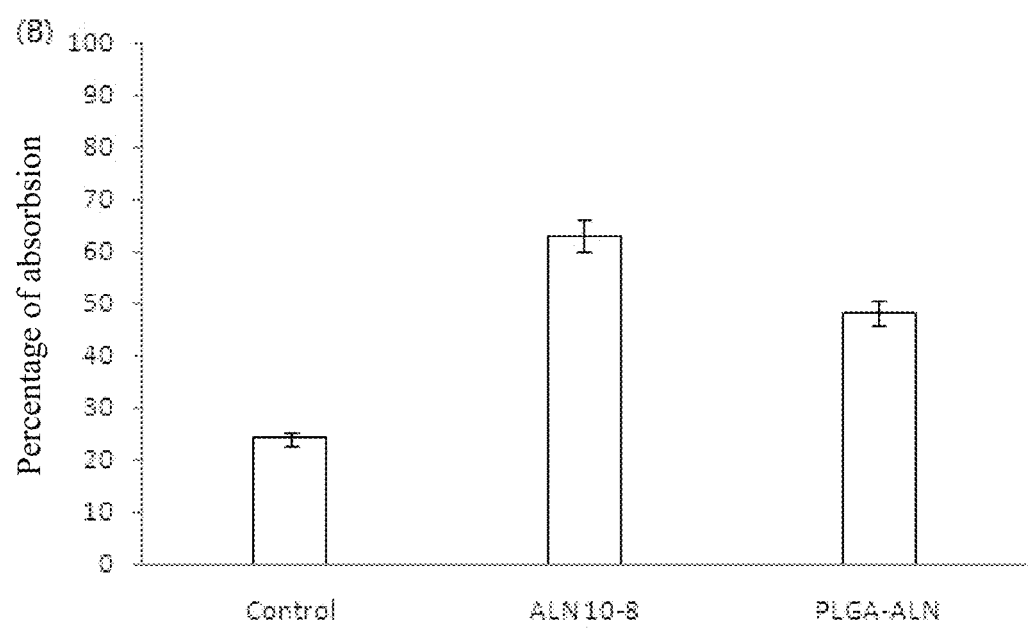

The ADSCs are seeded in PLGA-ALN-3D constructs at $10^5$ cells/well density followed by incubation for 12 h, and add the conditioned medium (DMEM supplemented with 10% FBS, 100 U/mL penicillin and 100 g/mL streptomycin) and cultured in incubator at 37° C., 5% $CO_2$, for 7 days. After 7 days the culture medium was changed into osteoinduction medium and change every 2-3 days, after 14 days the cells are fixed by using 4% of the paraformaldehyde and tested the osteogenesis using Alizarin red S staining. The Alizarin red S staining showed the higher mineralization after 7 and 14 days in PLGA-ALN-M treated hADSCs cultures compared to the non-treated control cultures (FIG. 4).

Example 10

Alizarin Red S Staining

Alizarin red S staining was used to determine the level of ECM (extra-cellular matrix) calcification 3 weeks after osteogenic induction. Cells were fixed with 4% paraformaldehyde at room temperature for 10 min. After washing once with $ddH_2O$, 1 mL Alizarin red S solution (1% in $ddH_2O$, pH 4.2) was added to each well in the 12-well plate. The staining solution was removed 10 min later, and each well was washed with $H_2O$ for 4-5 times. The fixed and stained plates were then air-dried at room temperature. The amount of mineralization was determined by dissolving the cell-bound alizarin red S in 10% acetic acid, and quantified spectrophotometrically at 415 nm.

Example 11

Osteogenic Differentiation of hADSCs

Figure 5:
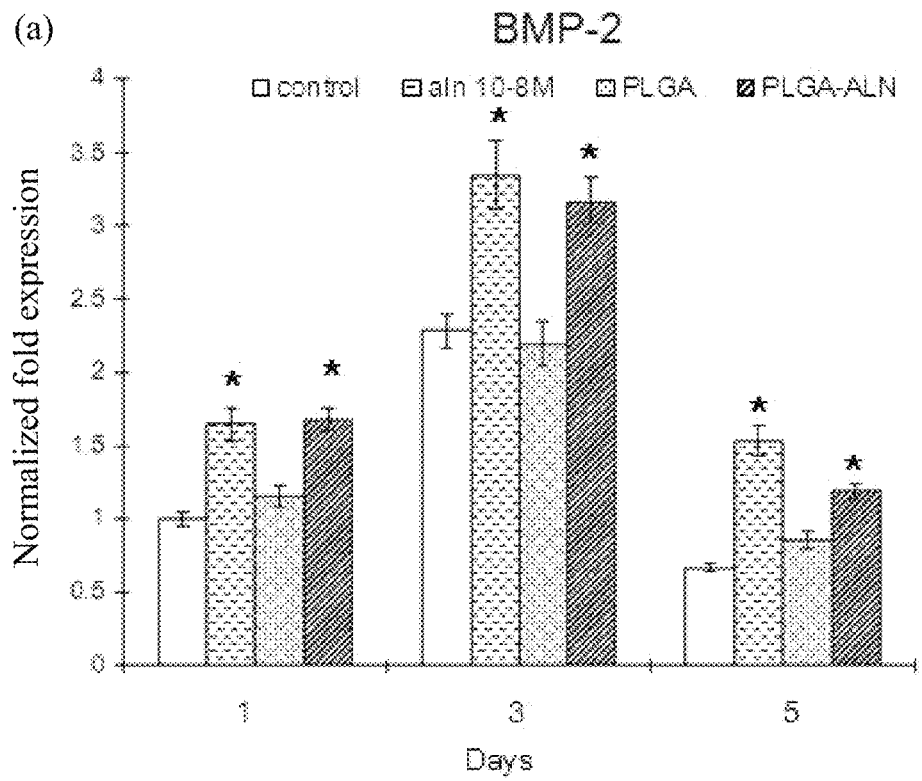
FIG. 5 shows RT-PCR analysis for osteogenic gene expressions in PLGA-ALN-M cultured hADSCs.
Figure 5:
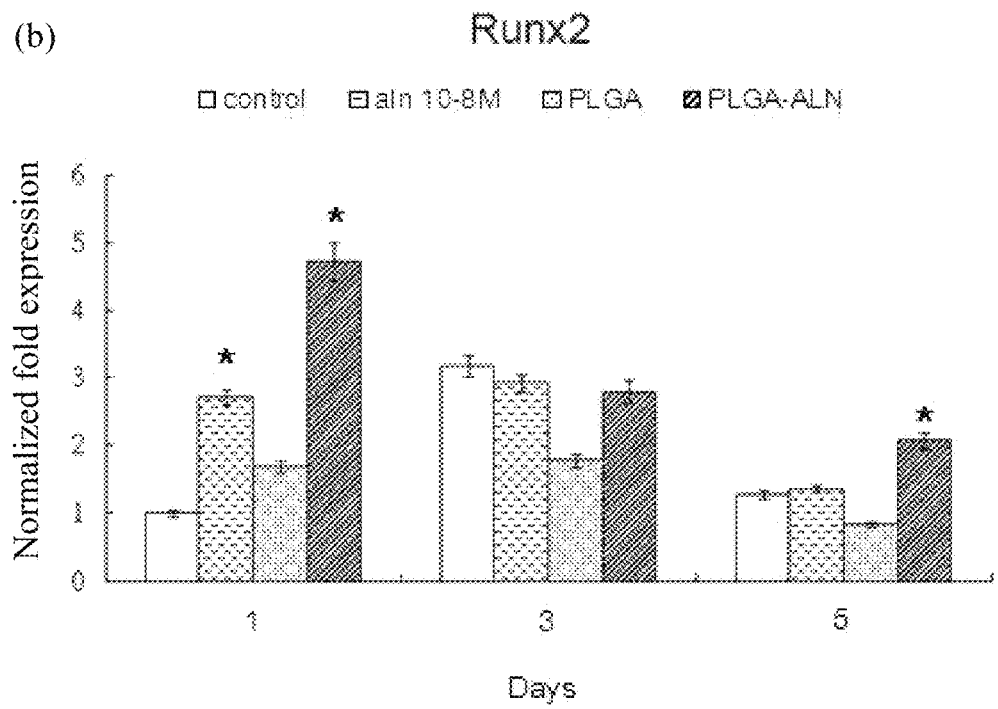
Figure 5:
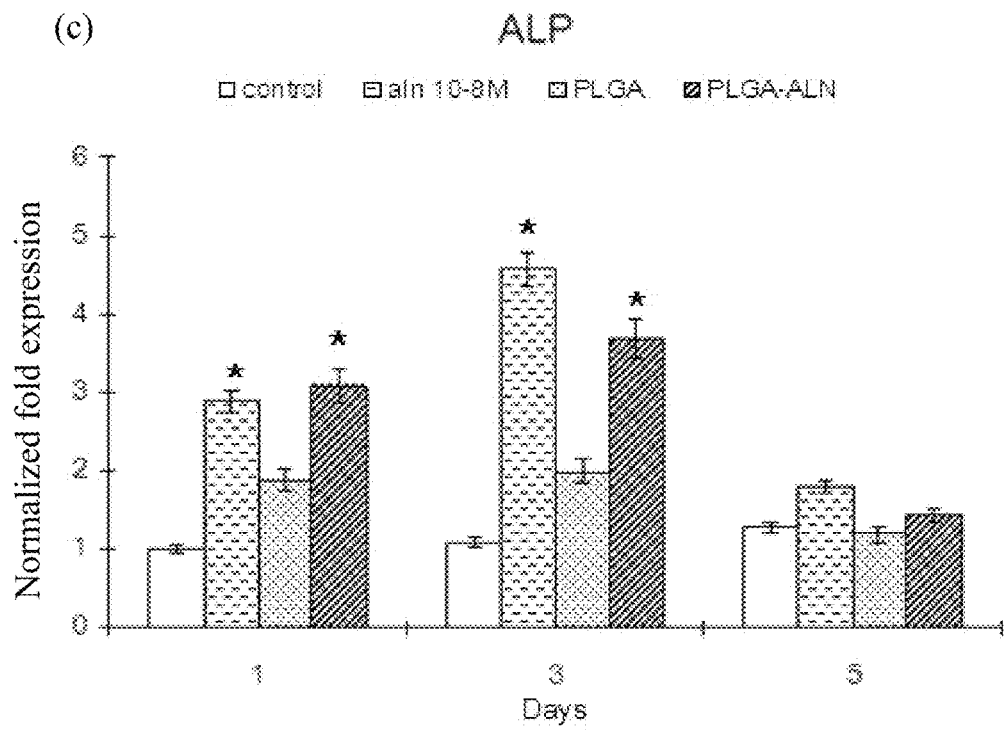
Figure 5:
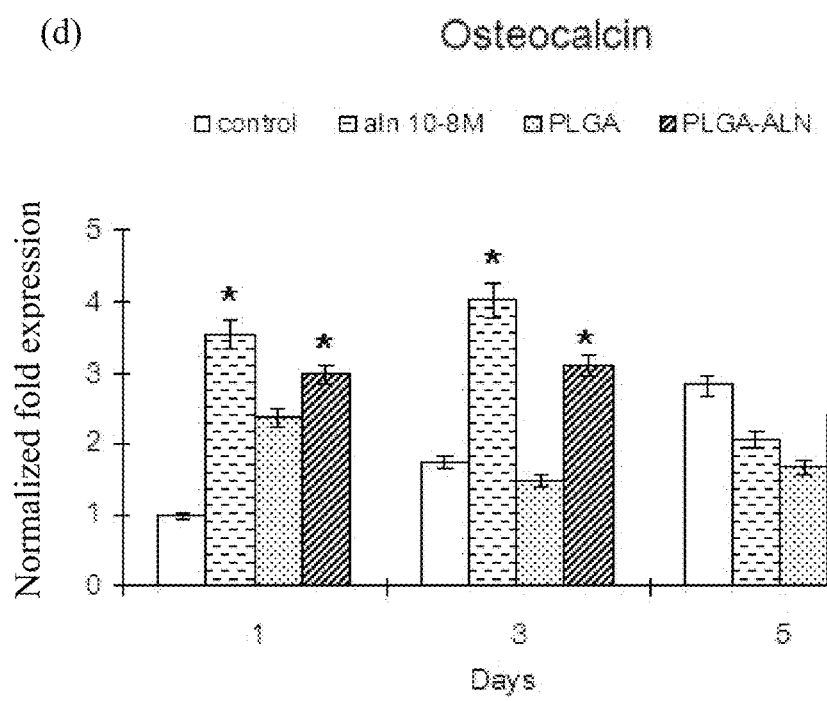
Figure 6:
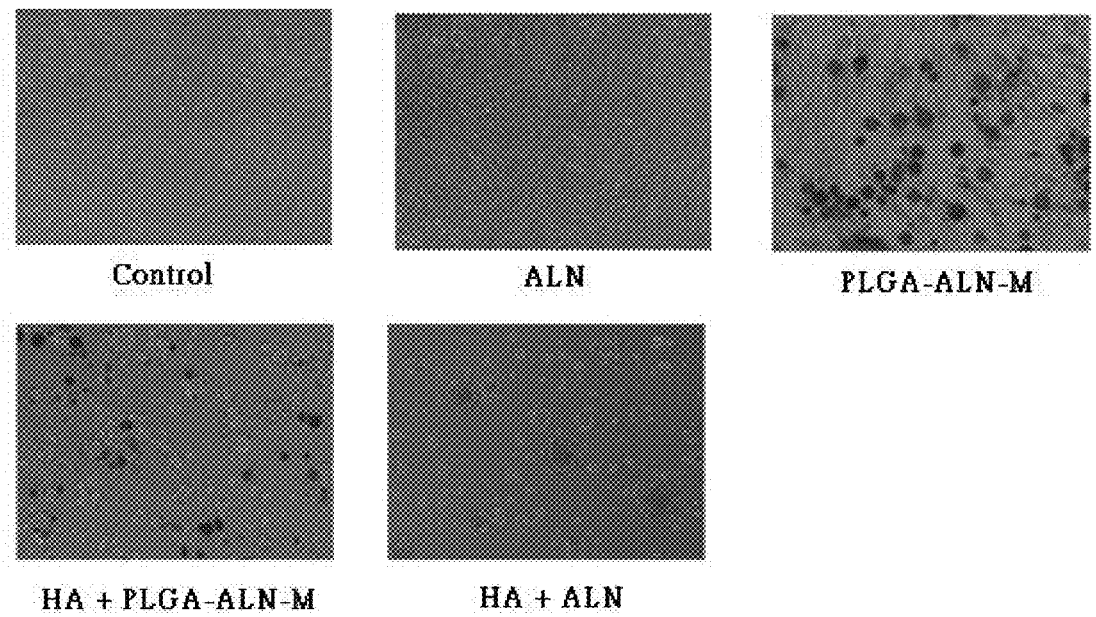
FIG. 6 shows that treatment of PLGA-ALN-M enhances chondrogenesis through the aggregation of hADSCs cultured under HA microenvironment for 2 hr.

To evaluate osteogenic differentiation of hADSCs, mRNA expressions of osteogenic marker genes (Osteocalcin, Alkalinephosphatase, Runx2 and BMP-2) from cells cultured on scaffolds are examined by using real time PCR. The mRNA expressions of osteogenic marker genes osteocalcin, BMP-2, Alkalinephosphatase (ALP), and Runx2, were significantly increased (p>0.05) in 1, 3 and 5 days of PLGA-ALN-M treatment in hADSCs cultures in comparison with the control culture (FIG. 5).

Example 12

Chondrogenic Differentiation

The ADSCs are seeded in an HA pre-coated 24 well plate, which was fitted with trans-well, at $10^5$ cells/well density and incubated for 2 h standing to form three-dimensional high-density micromass. 20 µL of PLGA-ALN-M (100 mg/mL) were treated through the trans-well. Conditioned medium was then added (DMEM/10% FBS, 50 nM ascorbate-2-phosphate, 1% antibiotic/antimycotic), and the plate was cultured in incubator at 37° C., 5% $CO_2$, for 14 days. After 7 days the trans-well with PLGA-ALN-M was removed and the culture medium was changed every 2-3 days.

Example 13

RNA Isolation and Real-time Polymerase Chain Reaction (Real-time PCR)

Figure 7:
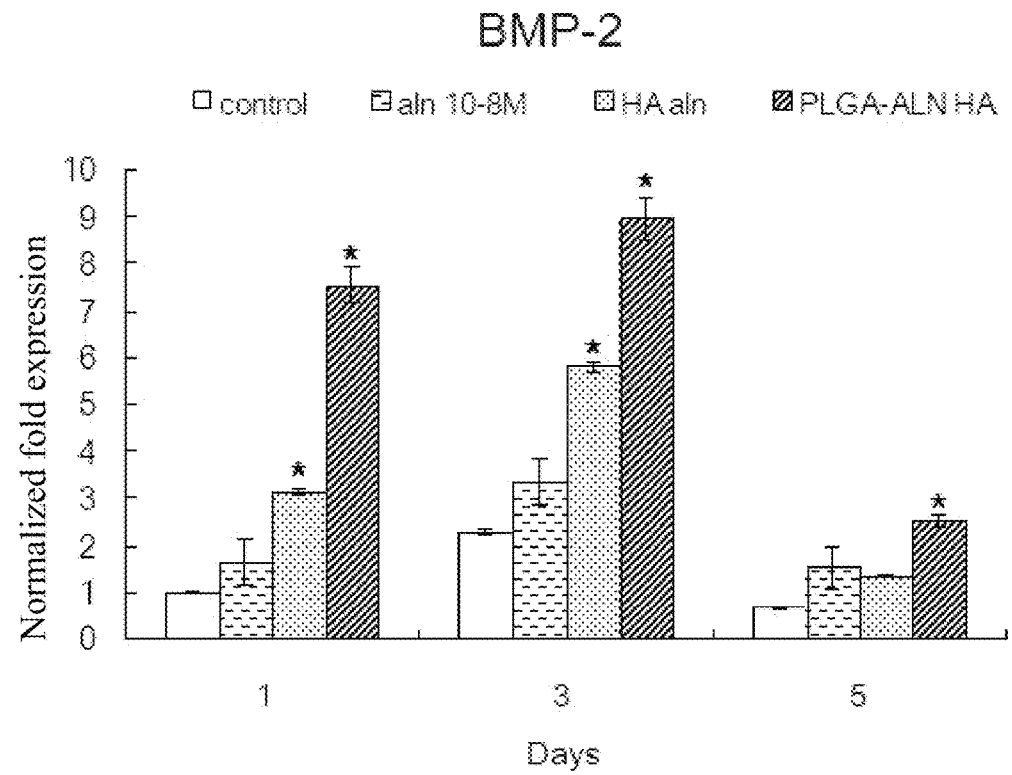
FIG. 7 shows chondrogenic gene expressions of (a) BMP-2, (b) SOX-9, (c) Type II collagen and (d) Aggrecan in PLGA-ALN-M treated hADSCs.
Figure 7:
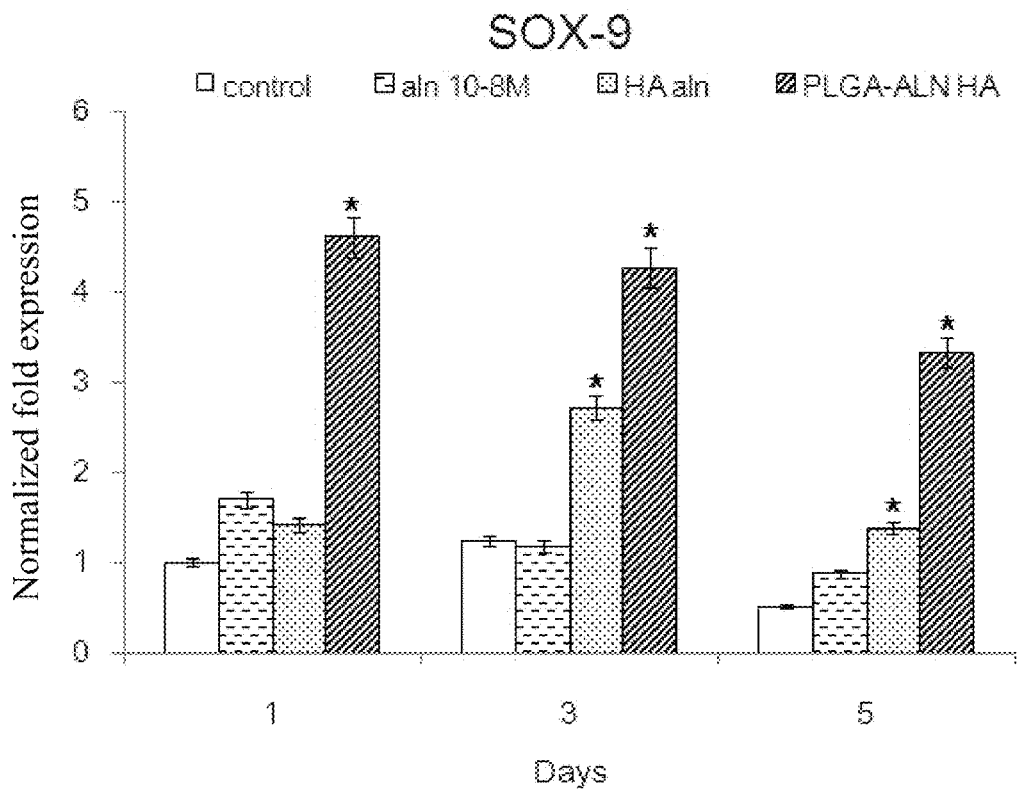
Figure 7:
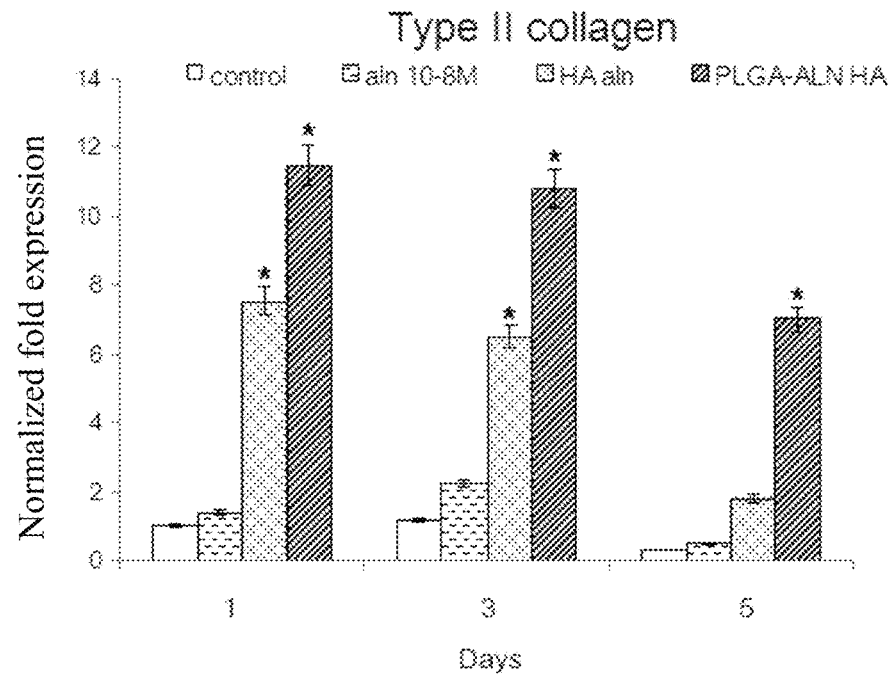
Figure 7:
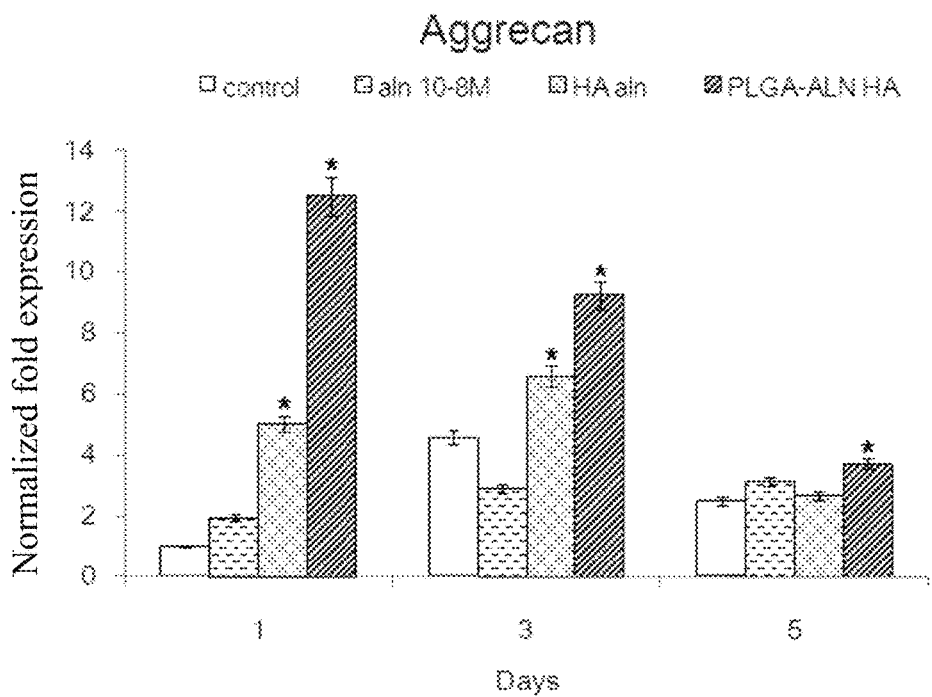

At indicated time intervals, cells were collected from cells/scaffold constructs. RNA extracting reagent TRIZOL (Gibco BRL, Rockville, Md.) was used to extract the total RNA from these cells by following manufacturer instructions. Briefly, 0.5-1 µg of total RNA in 20 µL of reaction volume were reverse transcribed into cDNA using the SUPERSCRIPT first-strand synthesis system (Invitrogen). Real-time PCR reactions were performed and monitored using the IQ SYBR GREEN real-time PCR supermix (Bio-Rad Laboratories Inc, Hercules, Calif.) and quantitative real-time PCR detection system (Bio-Rad Laboratories Inc, Hercules, Calif.). The cDNA samples (2 µL, the total volume of each reaction was 25 µL) were analyzed for gene of interest and the reference gene glyceraldehyde-3-phosphate-dehydrogenase (GAPDH). The expression level of each target gene was then calculated as $2^{-\Delta\Delta Ct}$, as previously described (Livak and Schmittgen, Methods, 2001, 25 (4): 402-408). Four readings of each experimental sample were performed for each gene of interest, and experiments were repeated at least three times. The mRNA expressions of osteogenic marker genes osteocalcin, BMP-2, Alkalinephosphatase (ALP), and Runx2, were significantly increased (p>0.05) in 1, 3 and 5 days of PLGA-ALN-M treatment in hADSCs cultures in comparison with the control culture (FIG. 5). The mRNA expressions of chondrogenic marker genes such as BMP-2, SOX-9, collagen type II, and Aggrecan for chondrogenesis were significantly increased (p>0.05) in 1, 3, and 5 days on PLGA-ALN microspheres treated hADSCs cultured under HA microenvironment in comparison with control culture (FIG. 7).

Example 14

Animals and Surgery

Figure 8:
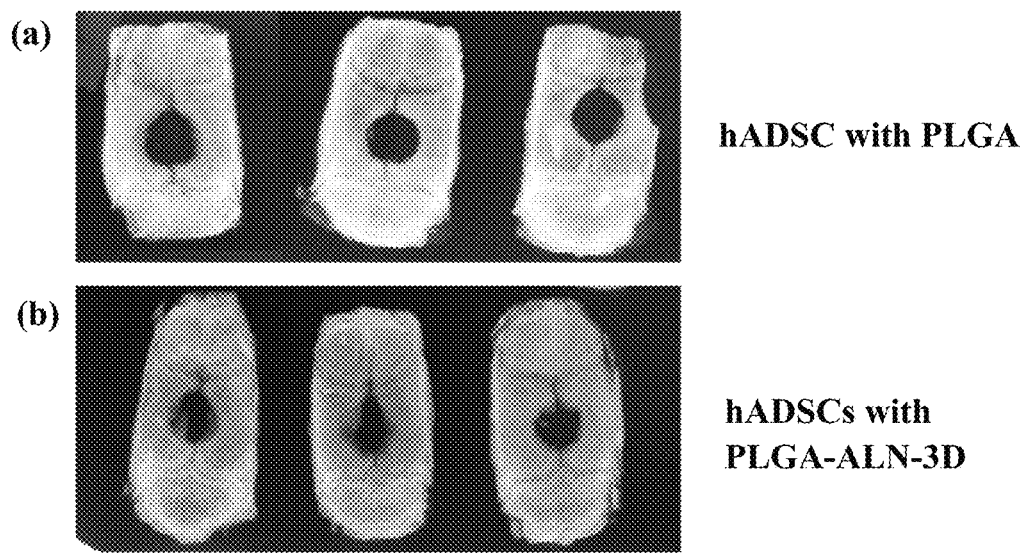
FIG. 8 shows radiographic images of hADSCs seeded (a) PLGA and (b) PLGA-ALN-3D treated rat calvarial defect after 8 weeks.
Figure 9:
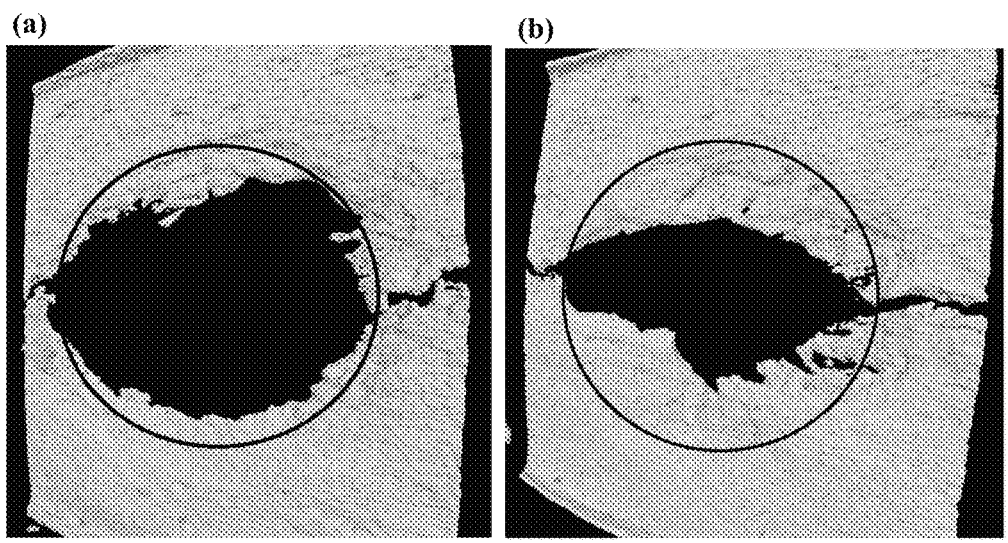
FIG. 9 shows micro CT analysis of hADSCs seeded (a) PLGA and (b) PLGA-ALN-3D treated rat calvarial defect after 8 weeks.

All animal experiments were performed in accordance with Kaohsiung Medical University Animal Care and Use Committee guidelines (IRB). Eighteen 8-10-week-old male Sprague Dawley rats (250-300 g) were housed in a light-and temperature-controlled environment and given food and water. Rats were anaesthetized with a combination of ketamine (75 mg/kg) and xylazine (10 mg/kg), administered intra-peritoneally. The dorsal part of the cranium was shaved, aseptically prepared for surgery, and a sagittal incision of approximately 20 mm opened over the scalp of the animal. The periosteum was removed and a full-thickness calvarial bone defect 5 mm in diameter was created using a slow speed dental drill without irrigation to heat damage the host bone on the rims and without damaging the dura. Bone defects were randomly implanted with hADSCs seeded PLGA-ALN-3D scaffolds or hADSCs seeded PLGA-3D scaffolds or left empty (n=6). Incisions were sutured and animals were allowed to recover for 8 weeks of post-surgery, after which they were sacrificed by $CO_2$ inhalation. To collect the implants, the skin was dissected, and the defect sites were removed along with surrounding bone. The specimens were fixed and prepared for micro CT analysis and histology analysis. The radiographic images showed that the PLGA-ALN-3D constructs showed the better bone in growth in defect site of rat calvaria eight weeks after implantation (FIG. 8). The micro CT observation showed that the bone formation in rat calvarial defect model treated with PLGA-ALN-3D contracts showed better effect after eight weeks (FIG. 9).

Example 15

Histological and Immunochemical Analysis

To assess cell morphology and the presence of cartilage-specific matrix proteins, cells/scaffold constructs were fixed overnight in 4% paraformaldehyde in PBS (pH 7.4) at 4° C. and transferred to 70% ethanol until processing. Constructs were embedded in paraffin, and cut into 5 μM. For histological analysis, sections were stained with Alcian blue for the presence of cartilage glycosaminglycan depositions. For immunohistochemistry, sections were also labeled with specific primary antibodies for collagen type II (dilution 1/100; Chemicon) followed FITC anti-mouse secondary antibodies (dilution 1/200; molecular probe). For negative control experiments, the primary antibodies were omitted. The sections were counterstained with 4',6-Diamidino-2-phenylindole (DAPI) (dilution 1/500; Sigma) to identify cellular nuclei that reflected the cell number.

Example 16

Animals and Experimental Design

The rats were divided into three groups, PLGA 10 mg, PLGA-ALN 5 mg, and PLGA-ALN 10 mg. For anesthesia, an intraperitoneal injection with a mixture of ketamin hydrochloride (100 mg/ml per 80 mg/kg body weight) and xylazin 2% (12 mg/kg body weight) were used. The left thigh was shaved and a 3 cm lateral longitudinal skin incision was made. The lateral approach was performed posterior to vastus lateralis without damaging the muscle. A bone defect, 0.1 cm×0.4 cm in size, on left femur was created at middle portion of shaft by using a 0.5 mm cone-shape bur. After that, the implant was inserted into the cavity and covered with SURGICEL™ (Johnson & Johnson Medical Limited, Neuchatel, Switzerland) to fix the implant in place. Radiographs were taken to verify the correct position of the bone defect using the great trochanter as control point. At the end of operation, skin wounds were sutured. Six weeks after operation, animals were sacrificed for biomechanical and histological analysis.

Example 17

Bone Defect Model Creation and Biomechanical Property Evaluation

Figure 10:
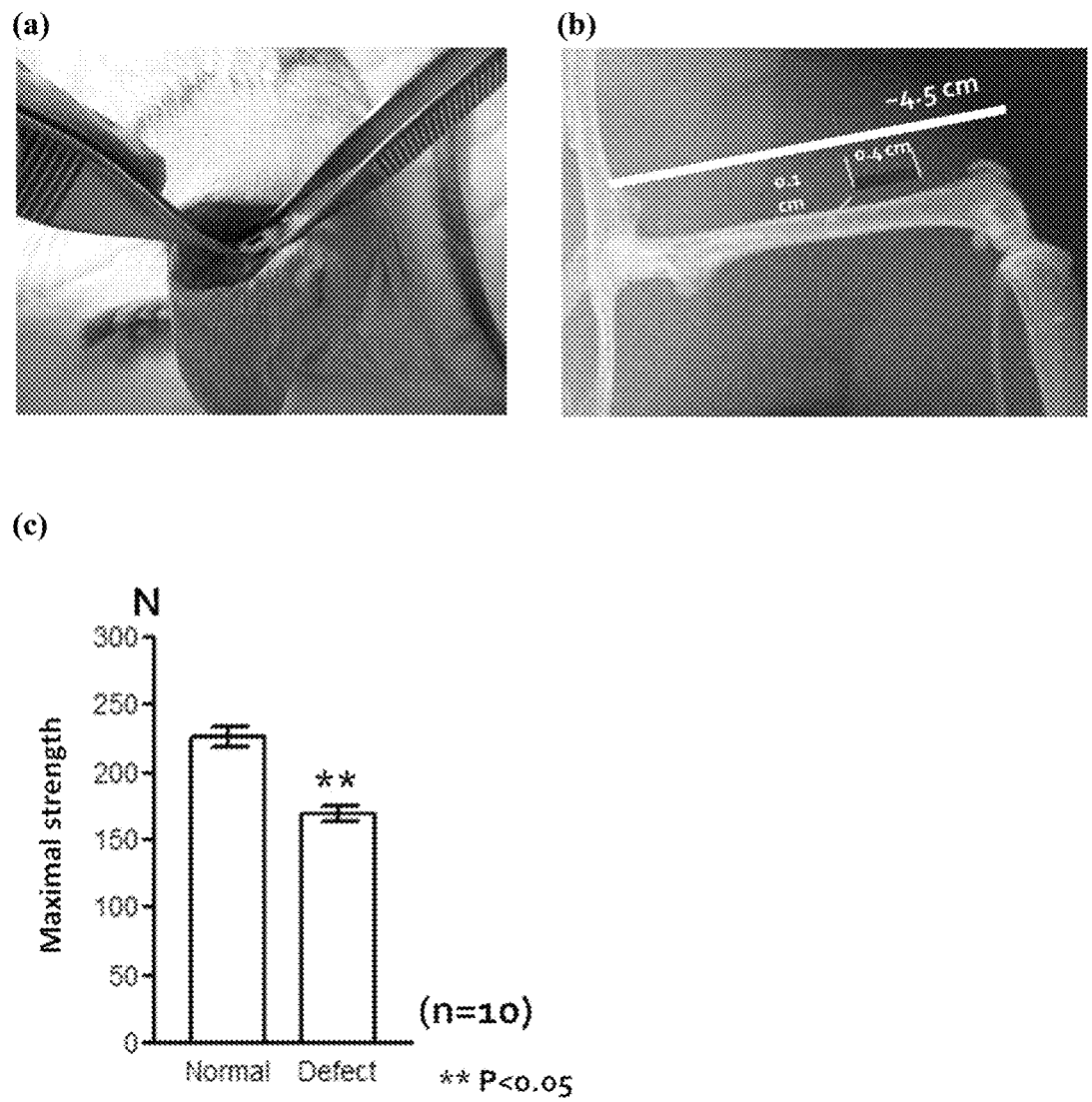
FIG. 10 shows the creation of femur bone defect model. (a) picture during operation, arrow indicates the defect site. (b) X-ray film and carton, which indicate the defect size and site. (c) mechanical property test on femur bone with or without defect performed by 3-point bending test. $P<0.05$

The present invention created a defect on the femoral diaphysis of rats (FIG. 10 (a) and (b)), and filled in the PLGA-ALN microsphere. Defect creation with over 5 mm in length might result in femoral bone fracture. The present invention employed 3-point bending test to analyze the mechanical property at the end of experiment. Counterlateral femoral bone served as a non-defect femoral bone. The present invention found that defect reduced the maximal strength from 226.1±6.2 to 171.6±4.8 N (p<0.05) (FIG. 10 (c)).

Mechanical property of bone: 3-point bending test: For testing the mechanical property of the repaired femoral defect, the Instron 4466 (model 4465; Instron, Canton, Mass.) was employed for mechanical tests. The rat femur was removed from body and all the connective tissues were stripped off. For 3-point bending, the femur bone was positioned onto two supports, and a single-pronged loading device was applied to the opposite surface at a point precisely in the middle between the two supports. The distance between two supports was 4 cm. Loading force was 1N with speed of 1 mm/min. The experimental procedure involved the measurement of the deflection of the bone at the point of load application and the concurrent measurement of the load, yielding a force-deflection graph. Parameters obtained from this graph include whole-bone stiffness (defined as the slope of the early, linear portion of the load-deflection curve), yield point, maximal load and fracture load. The Young's modulus of the material from the geometry of the loading device and the stiffness of the bone were measured. The data calculations were all based on beam theory and the Hooke's law.

Figure 11:
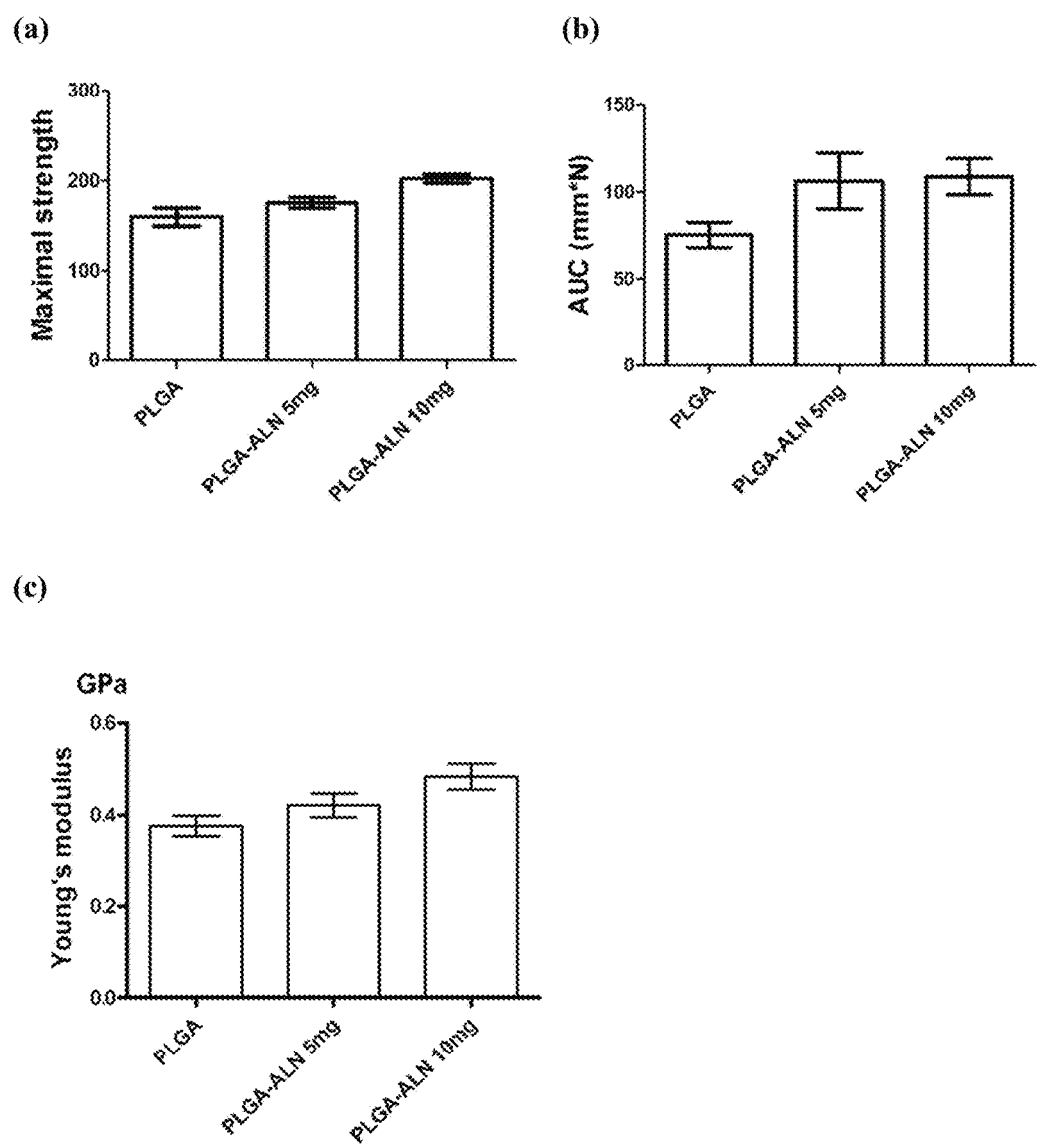
FIG. 11 shows mechanical property analysis by 3-point bending. (a) maximal strength (b) storage energy (c) Young's modulus. $P<0.05$ FIG. 12 show micro-CT images and trabecular bone volumn in defect site. (a) micro-CT 3D structure: a. PLGA alone group; b. PLGA-ALN 5 mg treatment and c. PLGA-ALN 10 mg treatment. Column 1: side view. Column 2: 45 degree rotation. Column 3: cross section at the middle of defect side. (b) image composition for all 3D images from column 1 and shows as cross section. (c) total new formed trabecular bone volumn were calculated and normalized with total length in bone marrow cavity.

Post-surgery for 6 weeks, the results of 3-point bending test showed that maximal strength in PLGA group (124±14.9N) was no significantly lower than that in PLGA-ALN 5 mg (172.5±18.2N) but 10 mg (191.7±11.7 N) groups (p<0.05) (FIG. 11 (a)). Total energy absorption were also reduced in PLGA group (74.99±6.43 mm*N) comparing with PLGA-ALN 5mg (106.43±15.36 mm*N) and significantly lower than PLGA-ALN 10mg (110.71±9.95 mm*N) groups (p<0.05) (FIG. 11 (b)). Young's modulus was also reduced in PLGA group (0.38±0.02 GPa) comparing with PLGA-ALN 5 mg (0.43±0.03 GPa) and 10 mg (0.51±0.03 GPa) groups (FIG. 11 (c)); however, there were no significant difference among groups. This concluded that PLGA-ALN increased maximal strength, Young's modulus, storage energy and in a dose-dependent manner in mechanical property.

Example 18

Micro-CT Experiment and Analysis

Animals were anesthesia during micro-CT images scanning. Small animal micro-CT (Skyscan 1076, Bruker, Belgium) was employed for analyzing bone repair process in living animals and calculated by image software (CTAn) at the desired time point. The scan conditions were set at an aluminum filter of 0.5mm, 35 μm scanning resolution, x-ray voltage of 50 KV, x-ray current of 200 mA and an exposure time of 600 m-seconds. The area used for analysis began at the defect site close to femoral head and through all the defect area. Total volume indicated the inner area of cortical bone. Trabecular bone volume indicated the total trabecular bone within the total volume. Trabecular bone volume was normalized with total defect length in each rat.

Figure 12:
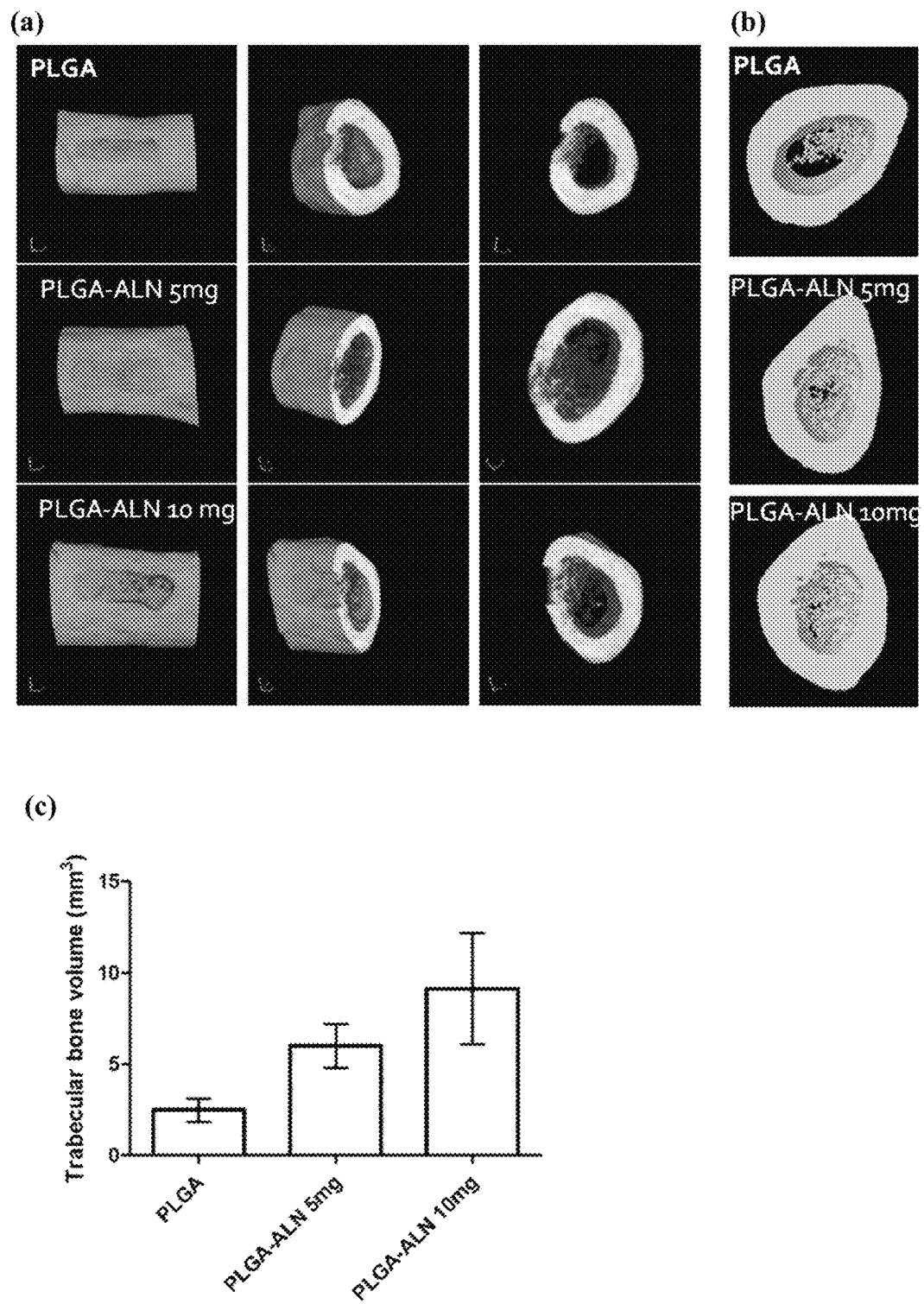
Figure 13:
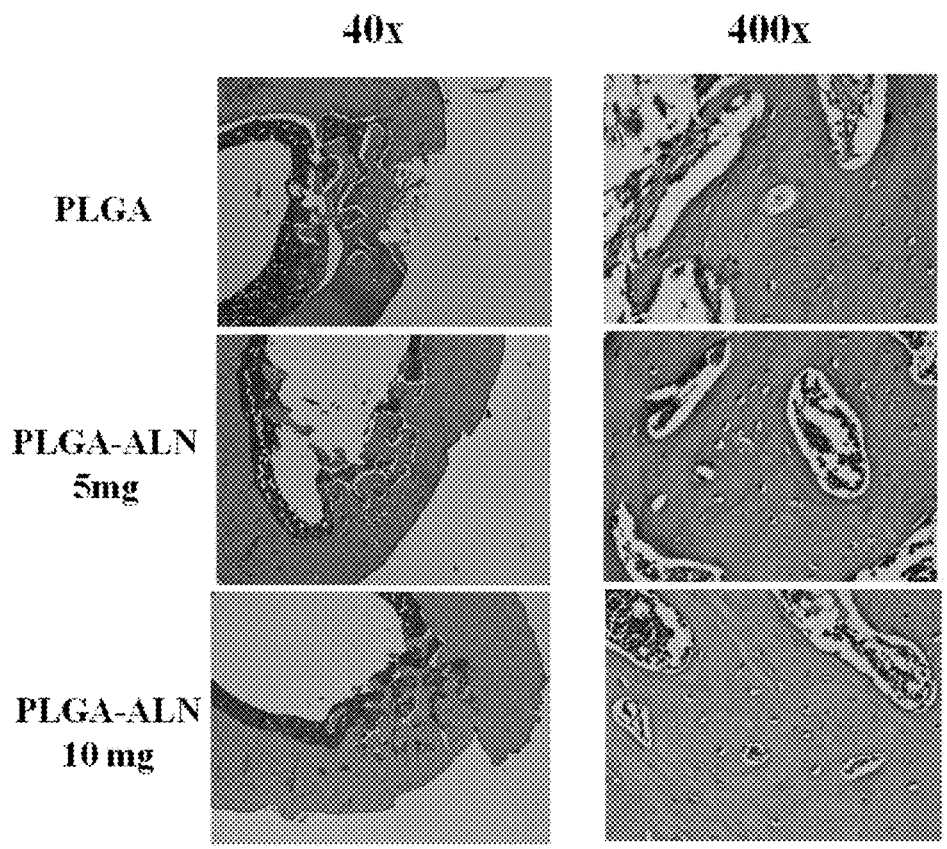
FIG. 13 shows histological analysis of the defect site of femoral bone section. (a) H&E stain. (b) Masson stain. There are three groups: a. PLGA alone group; b. PLGA-ALN 5 mg treatment group and c. PLGA-ALN 10 mg treatment group.
Figure 13:
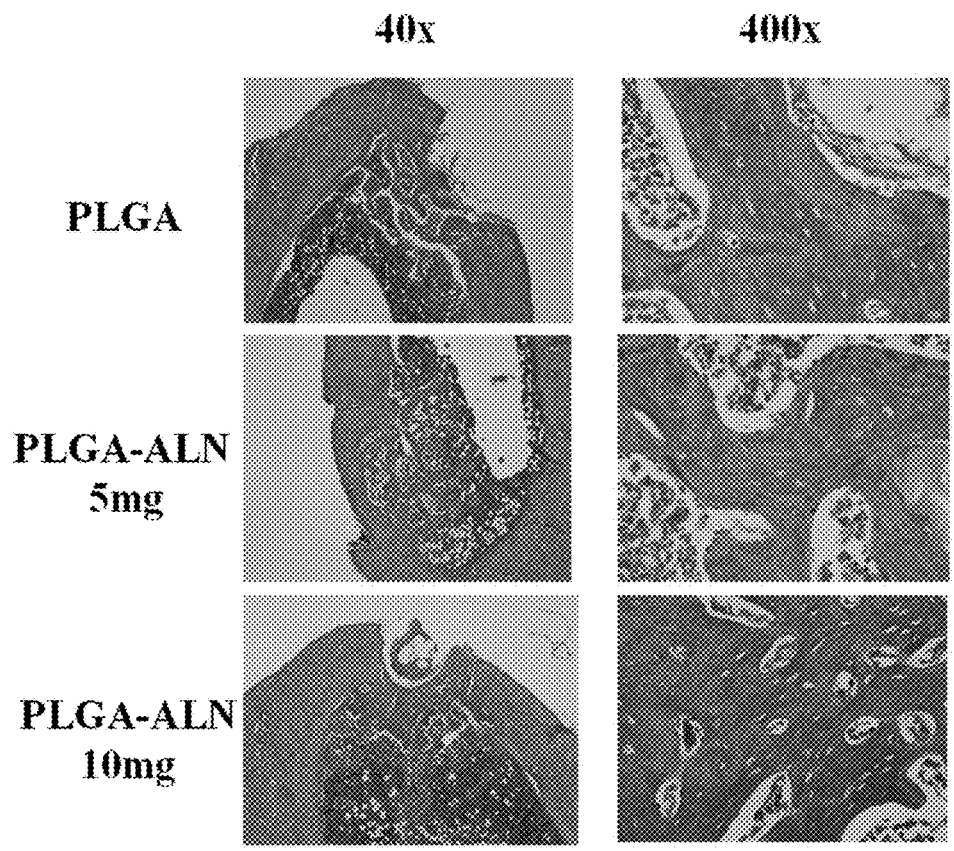

The micro-CT images on the defect area at 6 weeks after surgery were shown in FIG. 12 (a). From the lateral view, the present invention found that massive trabecular bone were found in the bone marrow cavity in PLGA-ALN groups, which indicated the new bone formation on the defect site from the 45 degree or cross section views (FIG. 12 (b)). The trabecular bone volumes from image sections were measured by the micro-CT software (CTAn) (FIG. 12 (c)). The present invention found that PLGA-ALN 5mg (1.413±0.21 trabecular bone volumes) and PLGA-ALN 10 mg (1.45±0.35 trabecular bone volumes) groups showed 2 times of trabecular bone volume than the control (0.71±0.17 trabecular bone volumes) or PLGA group (0.74±0.26 trabecular bone volumes) in the femoral defect site. The results showed that PLGA-ALN treatment enhanced the trabecular bone formation.

Example 19

Histological Experiment and Analysis

Femoral bone specimens were harvested for histological study 6 weeks after implantation. All specimens were decalcified, fixed and paraffin-embedded, as described previously. The 5-mm thick bone sections were removed and stained with hematoxylin and eosin (H&E; Santa Cruz, Santa Cruz, Calif., USA). A microscope with 10×, 100×, 400× magnification, equipped with a digital CCD camera (Eclipse 50i; Nikon Inc., Mich., USA), were used for images of the sections.

The viable cells reside in the lacunae of the repaired bone in PLGA and PLGA-ALN treatment group (FIG. 12 (a)). This result indicated that PLGA or PLAG-ALN implantation did not affect the new bone formation process. Thicker cortical bone and more trabecular bone were found in the PLGA-ALN groups than those in PLGA group. There were no differences in fibril collagen staining by Masson staining among PLGA and PLGA-ALN groups, (FIG. 12 (b)) indicating PLGA-ALN did not alter the fibril collagen formation during new bone forming process.

Example 20

PLGA-ALN-induced BMP-2 in New Formed Bone

The 5 μm thick sections of femoral bone were incubated in 0.1% EDTA for 10 min at 100 degree for antigen retrieval. Immunohistochemistry (IHC) was performed using the Immuno Cruz Staining System (Santa Cruz). After incubating with 5% BSA/PBS (Sigma, Saint Louis, Mo., USA) blocking solution for 2 h at room temperature, sections were labeled with human-specific anti-BMP2 (dilution 1:50; Abcam) overnight at 4 degree in a humid chamber. After washing with PBS, sections were incubated with a biotinylated secondary antibody (Dako, Carpinteria, Calif.) for 1 h and then incubated with horseradish peroxidase-conjugated streptavidin (Dako, Carpinteria, Calif.) for 1 h. The reaction was developed using a 3,30-diaminobenzidine solution containing 0.01% hydrogen peroxide, which resulted in a brown color. Then, sections were counterstained with hematoxylin. IHC images were taken using a microscope equipped with a digital CCD camera (Eclipse 50i; Nikon Inc., MI, USA).

Figure 14:
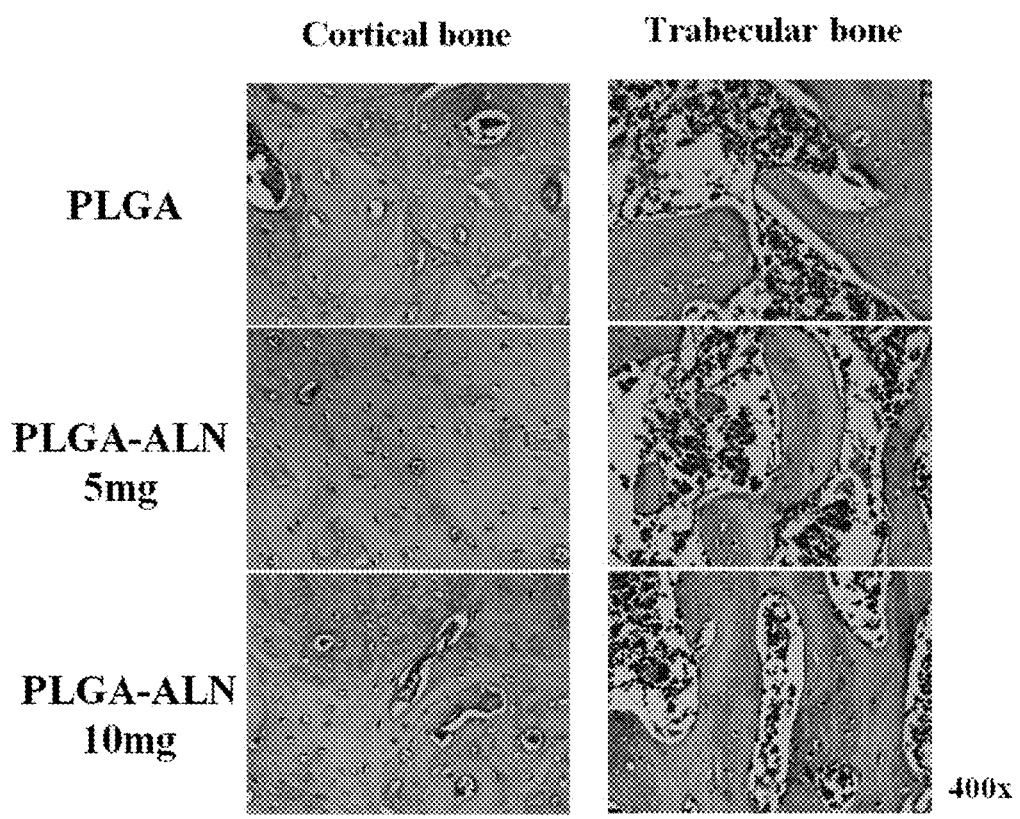
FIG. 14 shows the immuno-histochemistry analysis of the defect site of femoral bone section. BMP-2 level, left panel were taken from the cortical bone area and right panel were taken from the new formed trabecular bone area of defect side. There are three groups: a. PLGA alone group; b.

The results of immuno-histochemistry of BMP-2 showed that immunolocalized bone morphogenetic protein-2 (BMP-2) is predominant both in the repaired cortical bone and trabecular bone in PLGA-ALN groups rather than in PLGA group (FIG. 14). These results indicated that controlled-release ALN effectively increased BMP-2 level and further enhanced new bone formation on the defect site.

Example 21

Statistical Analysis

Three independent cultures for biochemical analysis were tested. Each experiment was repeated at least three times, and data (expressed as mean±SEM) from a representative experiment are shown. Statistical significance was evaluated by one-way analysis of variance (ANOVA), and multiple comparisons were performed by Scheffe's method. $p<0.05$ was considered significant. All values are expressed as the mean standard error of the mean (SEM) of at least three independent experiments. A one-way ANOVA (analysis of variance) was used to test for statistical differences, and multiple comparisons were performed using Scheffe's method. Statistical significance was set at $p<0.05$.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

What is claimed is:

1. A method for bone regeneration which comprises administering a sustained release composition comprising a poly(lactic-co-glycolic acid) cross-linked alendronate (PLGA-ALN) locally into an injured bone area of a subject suffering from bone injury, wherein the form of the PLGA-ALN is a PLGA-ALN-3D scaffold having a pore size of 150-300 μm or a PLGA-ALN-Microsphere having a diameter of 50-100 μm, and the administered concentration of the alendronate is controlled in such a manner that bone tissues of the injured bone area are exposed in situ to the alendronate in the concentration range of $5\times10^{-7}$ M to $5\times10^{-8}$ M over a period of 9 days.

2. The method of claim 1, wherein as compared to the bone tissues of the injured bone area of the subject before administering the sustained release composition comprising the PLGA-ALN-3D scaffold or the PLGA-ALN-Microsphere, the alendronate increases the rate of differentiation of stem cells of the bone tissues of the injured bone area into osteogenic cells that form bone.

3. The method of claim 1, wherein the alendronate increases the expression of bone morphogenetic protein-2 (BMP-2) to enhance the bone regeneration in the bone tissue.

4. The method of claim 1, wherein the bone tissues of the injured bond area are exposed in situ to the alendronate at a concentration of $5-7\times10^{-7}$ M at the first and second days after administering.

5. The method of claim 1, wherein the average porosity of the PLGA-ALN-3D scaffold is 85%.

6. The method of claim 1, wherein the bone injury is bone fracture.

* * * * *